(12) United States Patent
Schell et al.

(10) Patent No.: US 8,206,564 B2
(45) Date of Patent: Jun. 26, 2012

(54) BIOSENSOR CALIBRATION SYSTEM

(75) Inventors: Robert D. Schell, Goshen, IN (US);
Joseph E. Perry, Osceola, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 11/781,425

(22) Filed: Jul. 23, 2007

(65) Prior Publication Data

US 2009/0030617 A1    Jan. 29, 2009

(51) Int. Cl.
C12Q 1/00 (2006.01)
G01N 33/48 (2006.01)
(52) U.S. Cl. ............ 204/403.03; 702/19; 702/91; 435/4
(58) Field of Classification Search ............... 204/403.03
See application file for complete search history.

(56) References Cited

U.S. PATENT DOCUMENTS

| | | | |
|---|---|---|---|
| 4,714,874 A | 12/1987 | Morris et al. | |
| 5,281,395 A | 1/1994 | Markart et al. | |
| 5,445,967 A | 8/1995 | Deuter | |
| 5,510,266 A | 4/1996 | Bonner et al. | |
| 5,575,403 A | 11/1996 | Charlton et al. | |
| 5,856,195 A | 1/1999 | Charlton et al. | |
| 5,863,800 A | 1/1999 | Eikmeier et al. | |
| 6,599,406 B1 | 7/2003 | Kawanaka et al. | |
| 6,814,844 B2 | 11/2004 | Bhullar et al. | |
| 2003/0013941 A1 | 1/2003 | Cohn et al. | |
| 2004/0019653 A1 | 1/2004 | Debaty et al. | |
| 2004/0019686 A1 | 1/2004 | Toyoda et al. | |
| 2004/0156832 A1 | 8/2004 | Jolly | |
| 2004/0200721 A1 | 10/2004 | Bhullar et al. | |
| 2004/0244151 A1 | 12/2004 | Sakata et al. | |
| 2005/0016845 A1 | 1/2005 | Groll et al. | |
| 2005/0016846 A1 | 1/2005 | Groll et al. | |
| 2005/0019805 A1 | 1/2005 | Groll | |
| 2005/0019945 A1 | 1/2005 | Groll et al. | |
| 2005/0019953 A1 | 1/2005 | Groll et al. | |
| 2005/0023137 A1 | 2/2005 | Bhullar et al. | |
| 2005/0076845 A1 | 4/2005 | Langdale | |
| 2005/0079945 A1 | 4/2005 | Wittkopp | |
| 2005/0161345 A1 | 7/2005 | Groll et al. | |
| 2005/0168747 A1* | 8/2005 | Fox .............................. | 356/446 |

(Continued)

FOREIGN PATENT DOCUMENTS

EP    1152239    11/2001

(Continued)

OTHER PUBLICATIONS

EPO, "Search Report and Written Opinion for PCT/US2008/069408", Jan. 12, 2008, Publisher: International Searching Authority.

*Primary Examiner* — Jonathan C Teixeira Moffat
(74) *Attorney, Agent, or Firm* — Nixon Peabody LLP

(57) ABSTRACT

A biosensor system determines an analyte concentration using one or more calibrated correlation equations for an optical and/or electrochemical analysis of a biological fluid. The biosensor system may be implemented using a measurement device and a sensor strip. The measurement device senses circuit patterns on an encoding pattern of the sensor strip. The measurement device determines calibration information in response to the circuit patterns, and uses the calibration information to calibrate one or more of the correlation equations. The measurement device uses the calibrated correlation equations to determine the analyte concentration.

33 Claims, 18 Drawing Sheets

U.S. PATENT DOCUMENTS

| | | |
|---|---|---|
| 2005/0226846 A1 | 10/2005 | Umlauf et al. |
| 2005/0279647 A1 | 12/2005 | Beaty et al. |
| 2006/0189895 A1 | 8/2006 | Neel et al. |
| 2007/0015286 A1* | 1/2007 | Neel et al. .................... 436/149 |
| 2007/0110615 A1 | 5/2007 | Neel et al. |
| 2008/0105024 A1 | 5/2008 | Creaven et al. |
| 2008/0254544 A1* | 10/2008 | Modzelewski et al. ......... 436/43 |
| 2009/0113981 A1 | 5/2009 | Beer |
| 2009/0301166 A1 | 12/2009 | Charlton et al. |
| 2010/0022862 A1* | 1/2010 | Wang et al. .................. 600/345 |

FOREIGN PATENT DOCUMENTS

| | | |
|---|---|---|
| EP | 1256798 | 11/2002 |
| EP | 1475630 | 11/2004 |
| WO | WO 2004113914 | 12/2004 |
| WO | WO 2004113915 | 12/2004 |
| WO | WO 2005001474 | 1/2005 |
| WO | WO 2006035322 | 4/2006 |
| WO | WO 2006113723 | 10/2006 |
| WO | WO 2006113865 | 10/2006 |
| WO | 2009076263 | 6/2009 |

* cited by examiner

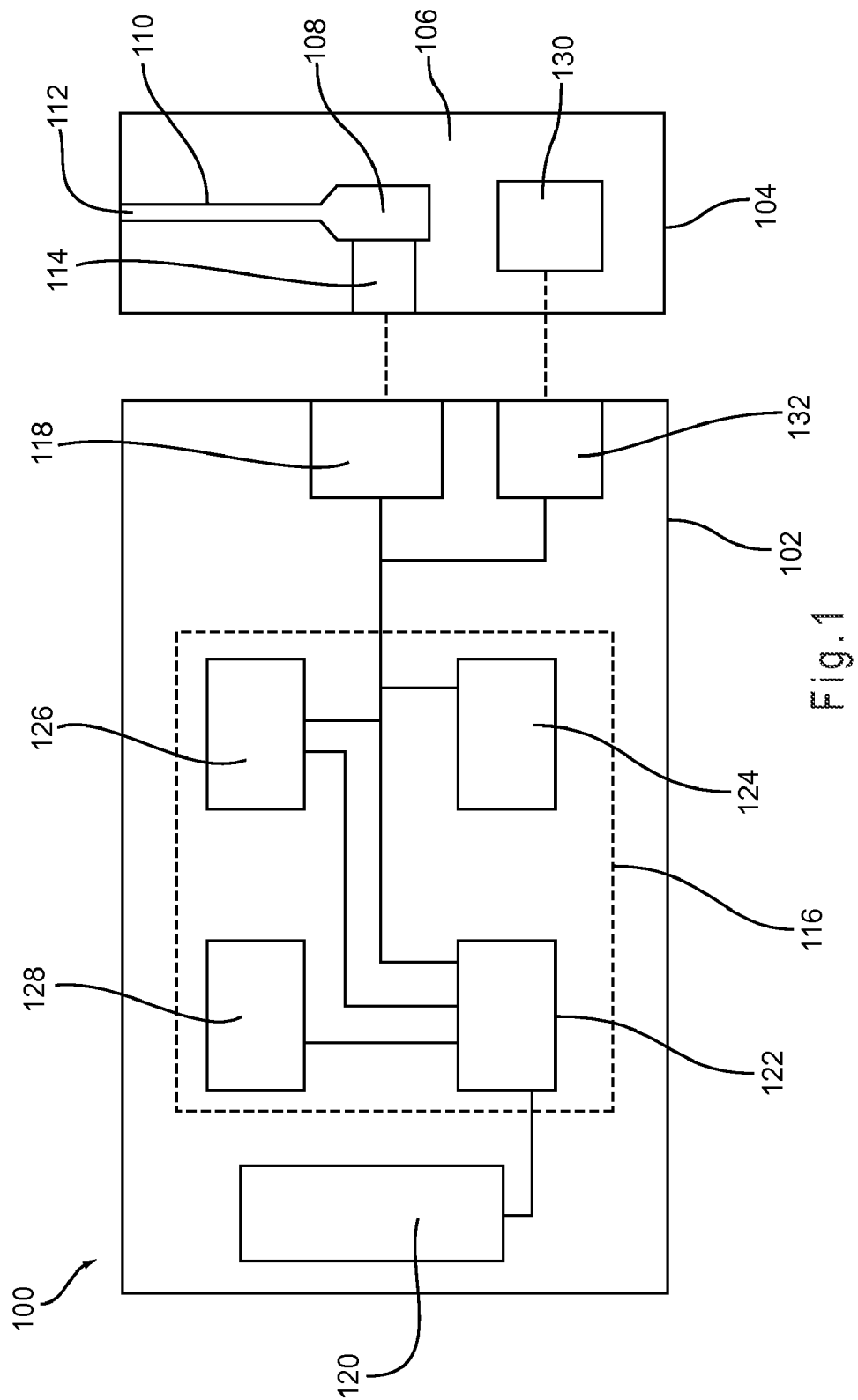

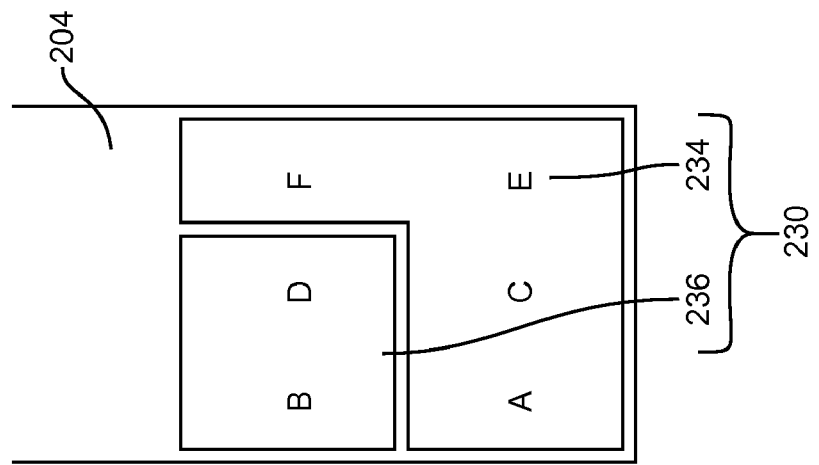
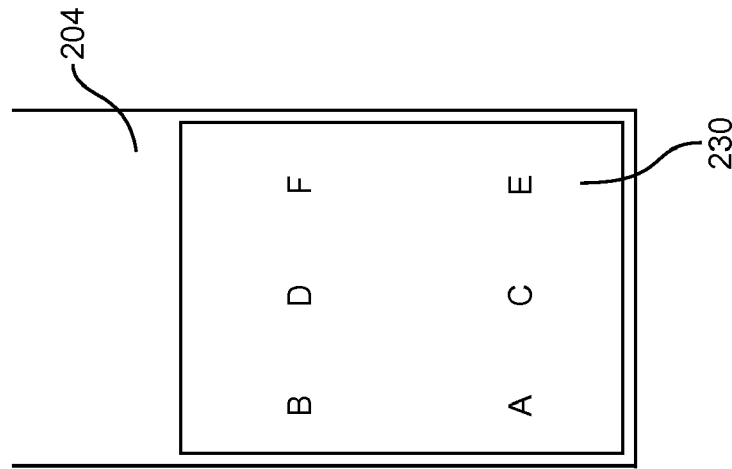
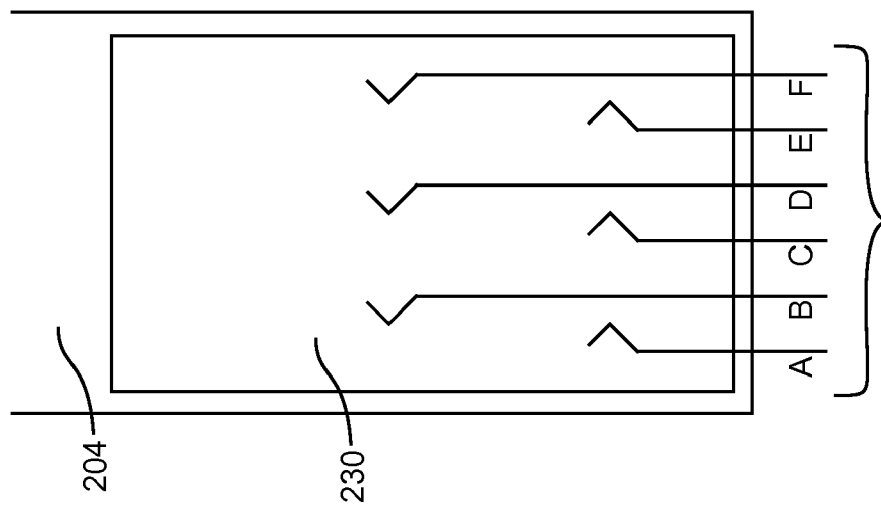

| Circuit Patterns | Digital Representation |
|---|---|
| 236, 234 — [1 0 0 / 1 0 0] | 6 5 4 3 2 1<br>0 0 0 0 1 1 |
| 236 — [1 1 0 / 0 0 0] —234 | 0 0 0 1 1 0 |
| 236 — [1 1 0 / 1 0 0] —234 | 0 0 0 1 1 1 |
| 236 — [0 1 1 / 0 0 0] —234 | 0 0 1 1 0 0 |
| 236 — [1 1 1 / 0 0 0] —234 | 0 0 1 1 1 0 |
| 236 — [1 1 0 / 1 0 0] —234 | 0 0 1 1 1 1 |
| 234 — [0 0 1 / 0 0 1] —236 | 0 1 1 0 0 0 |
| 234 — [0 1 1 / 0 0 1] —236 | 0 1 1 1 0 0 |
| 234 — [1 1 1 / 0 0 1] —236 | 0 1 1 1 1 0 |

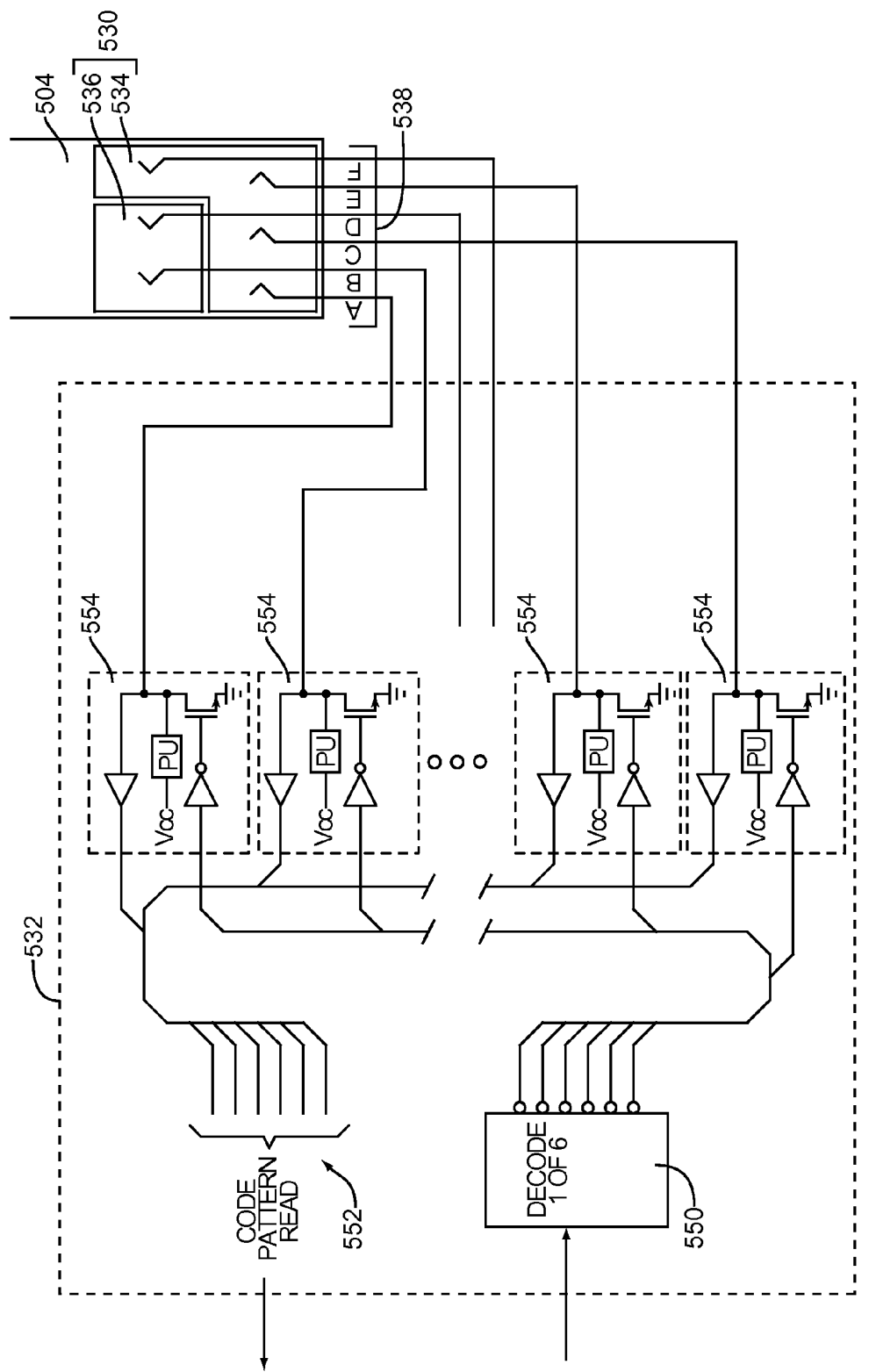

| Circuit Pattern | Digital Representation | Circuit Pattern | Digital Representation |
|---|---|---|---|
| | 8 7 6 5 4 3 2 1 | | 8 7 6 5 4 3 2 1 |
| | 0 0 0 0 0 0 1 1 | | 0 0 1 1 0 0 0 0 |
| | 0 0 0 0 0 1 1 0 | | 0 0 1 1 1 0 0 0 |
| | 0 0 0 0 0 1 1 1 | | 0 0 1 1 1 1 0 0 |
| | 0 0 0 0 1 1 0 0 | | 0 0 1 1 1 1 1 0 |
| | 0 0 0 0 1 1 1 0 | | 0 0 1 1 1 1 1 1 |
| | 0 0 0 0 1 1 1 1 | | 0 1 1 0 0 0 0 0 |
| | 0 0 0 1 1 0 0 0 | | 0 1 1 1 0 0 0 0 |
| | 0 0 0 1 1 1 0 0 | | 0 1 1 1 1 0 0 0 |
| | 0 0 0 1 1 1 1 0 | | 0 1 1 1 1 1 0 0 |
| | 0 0 0 1 1 1 1 1 | | 0 1 1 1 1 1 1 0 |

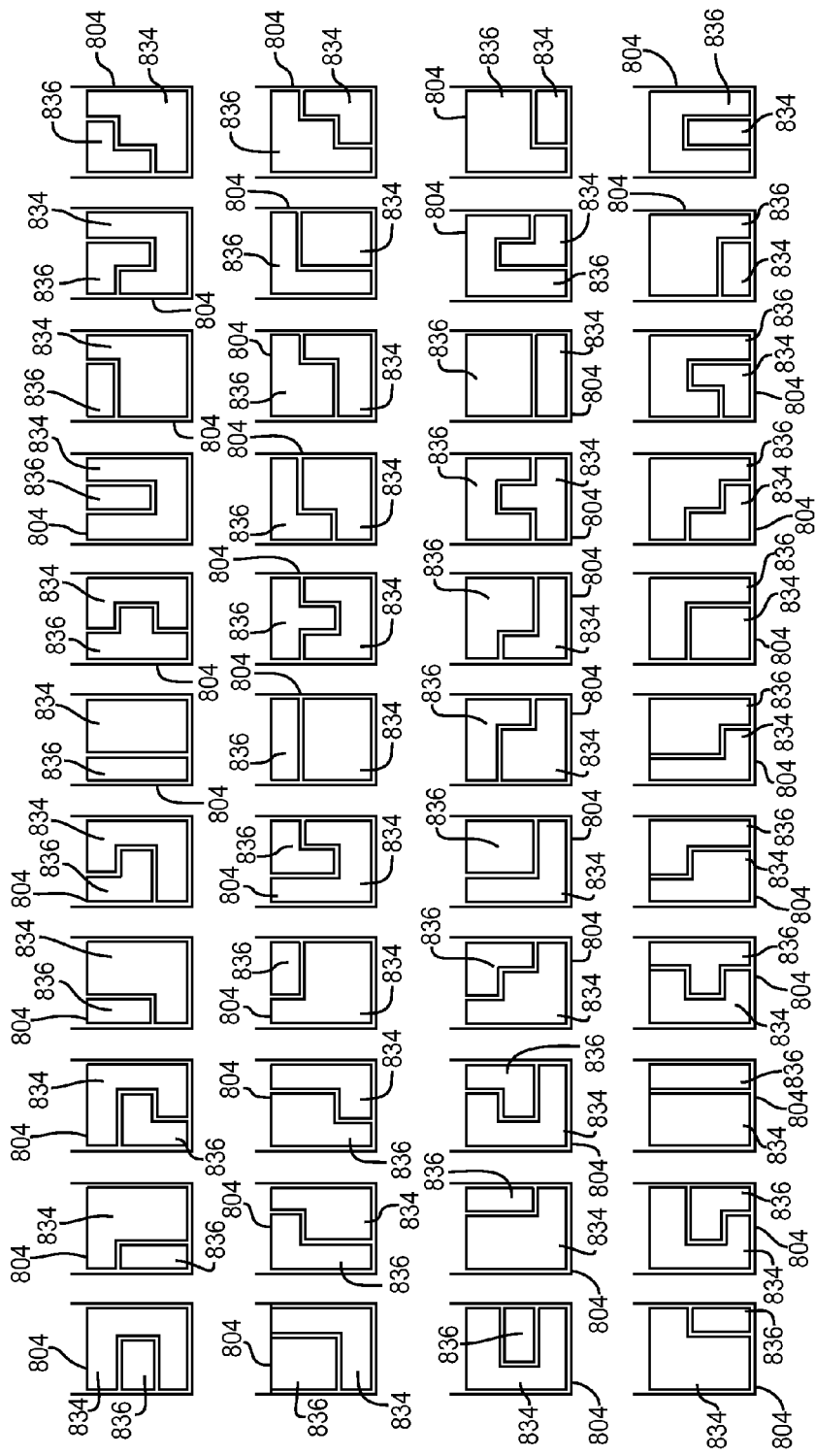

Fig.9A and Fig.9B

| Circuit Pattern | Digital Representation |
|---|---|

4 3 2 1

0 0 1 1

0 1 1 0

BIOSENSOR CALIBRATION SYSTEM

BACKGROUND

Biosensors provide an analysis of a biological fluid, such as whole blood, urine, or saliva. Typically, biosensors have a measurement device that analyzes a sample of the biological fluid placed in a sensor strip. The analysis determines the concentration of one or more analytes, such as alcohol, glucose, uric acid, lactate, cholesterol, or bilirubin, in a sample of the biological fluid. The sample of biological fluid may be directly collected or may be a derivative of a biological fluid, such as an extract, a dilution, a filtrate, or a reconstituted precipitate. The analysis is useful in the diagnosis and treatment of physiological abnormalities. For example, a diabetic individual may use a biosensor to determine the glucose level in whole blood for adjustments to diet and/or medication.

Many biosensor systems provide calibration information to the measurement device prior to the analysis. The measurement device may use the calibration information to adjust the analysis of the biological fluid in response to one or more parameters, such as the type of biological fluid, the particular analyte(s), and the manufacturing variations of the sensor strip. The accuracy and/or precision of the analysis may be improved with the calibration information. Accuracy may be expressed in terms of bias of the sensor system's analyte reading in comparison to a reference analyte reading, with larger bias values representing less accuracy, while precision may be expressed in terms of the spread or variance among multiple measurements. If the calibration information is not read properly, the measurement device may not complete the analysis or may make a wrong analysis of the biological fluid.

Biosensors may be designed to analyze one or more analytes and may use different volumes of biological fluids. Some biosensors may analyze a single drop of whole blood, such as from 0.25-15 microliters (µL) in volume. Biosensors may be implemented using bench-top, portable, and like measurement devices. Portable measurement devices may be hand-held and allow for the identification and/or quantification of one or more analytes in a sample. Examples of portable measurement systems include the Ascensia Breeze® and Elite® meters of Bayer HealthCare in Tarrytown, N.Y., while examples of bench-top measurement systems include the Electrochemical Workstation available from CH Instruments in Austin, Tex.

Biosensors may use optical and/or electrochemical methods to analyze the sample of the biological fluid. In some optical systems, the analyte concentration is determined by measuring light that has interacted with a light-identifiable species, such as the analyte or a reaction or product formed from a chemical indicator reacting with the analyte redox reaction. In other optical systems, a chemical indicator fluoresces or emits light in response to the analyte redox reaction when illuminated by an excitation beam. In either optical system, the biosensor measures and correlates the light with the analyte concentration of the biological sample.

In electrochemical biosensors, the analyte concentration is determined from an electrical signal generated by an oxidation/reduction or redox reaction of the analyte when an input signal is applied to the sample. An enzyme or similar species may be added to the sample to enhance the redox reaction. The redox reaction generates an electrical output signal in response to the input signal. The input signal may be a current, potential, or combination thereof. The output signal may be a current (as generated by amperometry or voltammetry), a potential (as generated by potentiometry/galvanometry), or an accumulated charge (as generated by coulometry). In electrochemical methods, the biosensor measures and correlates the electrical signal with the concentration of the analyte in the biological fluid.

Electrochemical biosensors usually include a measurement device that applies an input signal through electrical contacts to electrical conductors of the sensor strip. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes. The measurement device may have the processing capability to measure and correlate the output signal with the presence and/or concentration of one or more analytes in the biological fluid.

In many biosensors, the sensor strip may be adapted for use outside, inside, or partially inside a living organism. When used outside a living organism, a sample of the biological fluid is introduced into a sample reservoir in the sensor strip. The sensor strip may be placed in the measurement device before, after, or during the introduction of the sample for analysis. When inside or partially inside a living organism, the sensor strip may be continually immersed in the sample or the sample may be intermittently introduced to the strip. The sensor strip may include a reservoir that partially isolates a volume of the sample or be open to the sample. Similarly, the sample may continuously flow through the strip or be interrupted for analysis.

Sensor strips may include reagents that react with the analyte in the sample of biological fluid. The reagents may include an ionizing agent to facilitate the redox reaction of the analyte, as well as mediators or other substances that assist in transferring electrons between the analyte and the conductor. The ionizing agent may be an oxidoreductase, such as an analyte specific enzyme, which catalyzes the oxidation of glucose in a whole blood sample. The reagents may include a binder that holds the enzyme and mediator together.

Sensor strips may have one or more encoding patterns that provide calibration information to the measurement device. The calibration information may be identification information indicating the type of sensor strip, the analyte(s) or biological fluid associated with the sensor strip, the manufacturing lot of the sensor strip, or the like. The calibration information may indicate the correlation equations to use, changes to the correlation equations, or the like. Correlation equations are mathematical representations of the relationship between the electrical signal and the analyte in an electrochemical biosensor or between light and the analyte in an optical biosensor. Correlation equations may be implemented to manipulate the electrical signal or light for determination of the analyte concentration. Correlation equations also may be implemented as a program number assignment (PNA) table of slopes and intercepts for the correlation equations, another look-up table, or the like. The measurement device uses the calibration information to adjust the analysis of the biological fluid.

Many measurement devices obtain the calibration information from the encoding pattern either electrically or optically. Some encoding patterns may be read only electrically or only optically. Other encoding patterns may be read electrically and optically.

Electrical encoding patterns usually have one or more electrical circuits with multiple contacts or pads. The measurement device may have one or more conductors that connect with each contact on the encoding pattern of the sensor strip.

Typically, the measurement device applies an electrical signal through one or more of the conductors to one or more of the contacts on the encoding pattern. The measurement device measures the output signal from one or more of the other contacts. The measurement device may determine the calibration information from the absence or presence of output signals from the contacts on the encoding pattern. The measurement device may determine the calibration information from the electrical resistance of the output signals from the contacts on the encoding pattern. Examples of sensor strips with electrical encoding patterns may be found in U.S. Pat. Nos. 4,714,874; 5,856,195; 6,599,406; and 6,814,844.

In some electrical encoding patterns, the measurement device determines the calibration information from the absence or presence of different contacts. The contacts may be removed, never formed, or disconnected from other parts of the electrical circuit. If the measurement device measures an output signal from the location of a contact, then the measurement device presumes a contact is present. If the measurement device does not measure an output signal, then the measurement device presumes a contact is absent.

In other electrical encoding patterns, the measurement device determines the calibration information from the resistance of the electrical output signal from the contact. Typically, the amount of conductive material associated with each contact varies, thus changing the electrical resistance. Contacts may have additional or fewer layers of conductive material. The length and thickness of the connection between the contacts and the electrical circuit also may vary. The contacts may be removed, never formed, or disconnected from the electrical circuit.

Optical encoding patterns usually have a sequence of lines and/or array of pads. The measurement device determines the calibration information from the encoding pattern by scanning the encoding pattern to determine the absence or presence of the lines or pads.

Errors may occur with these conventional electrical and optical encoding labels. During manufacturing, shipping, handling, and the like, the sensor strips may acquire or lose material. The additional or missing material may cause the measurement device to obtain the wrong calibration information from the encoding label, which may prevent completion or cause a wrong analysis of the biological fluid.

In electrical encoding patterns, the additional or missing material may change or interfere with the calibration information. The additional material may cover the contacts, the contact locations, or the connections between the contacts. If the additional material is conductive, the measurement device may determine that a contact is present when a contact is absent or may measure an incorrect resistance from a contact. If the additional material is non-conductive, the measurement device may determine that a contact is absent when a contact is present or may measure an incorrect resistance from a contact. Additionally, the missing material may have been part of the contacts or the connections between the contacts. Thus, the missing material may cause the measurement device to determine that a contact is absent when a contact is present or may cause the measurement device to measure an incorrect resistance.

In optical encoding patterns, the additional or missing material may change or interfere with the calibration information. The additional material may cover or obstruct the lines or pads. The additional material may cover or obstruct the gaps or spaces between the lines or pads. The missing material may be part of the lines or pads. The additional or missing material may cause the measurement device to scan altered lines or pads.

Accordingly, there is an ongoing need for improved biosensors, especially those that may provide increasingly accurate and/or precise analyte concentration measurements. The systems, devices, and methods of the present invention overcome at least one of the disadvantages associated with encoding patterns on sensor strips used in biosensors.

SUMMARY

The present invention provides a biosensor system that calibrates an analyte analysis to determine an analyte concentration in a biological fluid. The biosensor system senses circuit patterns on a sensor strip. The circuit patterns provide calibration information, which the biosensor system may use to calibrate one or more correlation equations used in the analyte analysis. The analyte concentration is determined using one or more calibrated correlation equations.

A biosensor may have a measurement device and a sensor strip. The measurement device may have a processor connected to a pattern read device. The sensor strip may have an encoding pattern with two or more circuits. The measurement device and the sensor strip may implement an analyte analysis. The analyte analysis may have one or more correlation equations. The pattern read device may sense at least two circuit patterns on the encoding pattern of the sensor strip. The processor may determine calibration information in response to the circuit patterns. The processor may calibrate at least one correlation equation in response to the calibration information. The processor may determine an analyte concentration in response to one or more calibrated correlation equations.

Another biosensor may have a measurement device and a sensor strip. The measurement device may have a processor connected to a pattern read device. The pattern read device may have an array of electrical contacts. The sensor strip may have an encoding pattern. The encoding pattern may have at least two circuits and each circuit may have at least one contact area. The contact areas may be in electrical communication with the electrical contacts. The measurement device and sensor strip may implement an analyte analysis. The analyte analysis may have one or more correlation equations. The electrical contacts may selectively apply test signals to the contact areas on the encoding pattern. The pattern read device may sense at least two circuit patterns on the encoding pattern. The processor may determine calibration information in response to the circuit patterns. The processor may calibrate one or more correlation equations in response to the calibration information. The processor may determine an analyte concentration in response to one or more calibrated correlation equations.

In a method for calibrating an analysis of an analyte in a biological fluid, at least two circuit patterns on an encoding pattern are sensed. Calibration information is determined in response to the circuit patterns. One or more correlation equations are calibrated in response to the calibration information. An analyte concentration is determined in response to one or more calibrated correlation equations.

BRIEF DESCRIPTION OF THE DRAWINGS

The invention may be better understood with reference to the following drawings and description. The components in the figures are not necessarily to scale, emphasis instead being placed upon illustrating the principles of the invention.

FIG. 1 depicts a schematic representation of a biosensor system.

FIG. 2A depicts an array of electrical contacts in electrical communication with an encoding pattern.

FIG. 2B depicts the encoding pattern of FIG. 2A prior to the division of the encoding pattern into separate circuits.

FIG. 2C depicts the encoding pattern of FIG. 2A after division of the encoding pattern into separate circuits.

FIG. 5 depicts a pattern read device.

FIG. 8A depicts another undivided encoding pattern.

FIG. 8B depicts unique circuit patterns that may be disposed on the encoding pattern in FIG. 8A.

FIG. 9A depicts a numbering sequence of the contact areas of the encoding pattern in FIGS. 8A-B.

FIG. 9B depicts circuit patterns and respective digital representations of the circuits of FIG. 8B.

DETAILED DESCRIPTION

Figure 3A:
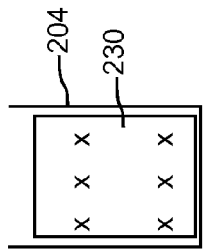
FIG. 3A depicts an undivided encoding pattern with contact areas X in electrical communication with an array of electrical contacts.

A biosensor system calibrates an analyte analysis to determine an analyte concentration in a sample of a biological fluid. The biosensor system has a measurement device that applies test signals to an encoding pattern on a sensor strip. The measurement device senses circuit patterns on the encoding pattern in response to the test signals. The circuit patterns provide calibration information, which the biosensor system uses to calibrate an optical and/or electrochemical analysis of the analyte in the biological fluid. The measurement device uses the calibration information to calibrate one or more correlation equations used in the analysis of the analyte. The measurement device determines the analyte concentration using one or more of the calibrated correlation equations.

FIG. 1 depicts a schematic representation of a biosensor system 100 that determines an analyte concentration in a sample of a biological fluid. The biosensor system 100 includes a measurement device 102 and a sensor strip 104. The measurement device 102 may be implemented as a bench-top device, a portable or hand-held device, or the like. The measurement device 102 and the sensor strip 104 may implement an analyte analysis, which may be an electrochemical analysis, an optical analysis, a combination thereof, or the like. The biosensor system 100 may determine analyte concentrations, including those of alcohol, glucose, uric acid, lactate, cholesterol, bilirubin, and the like in biological samples such as whole blood and urine. While a particular configuration is shown, the biosensor system 100 may have other configurations, including those with additional components.

The sensor strip 104 has a base 106 that forms a sample reservoir 108 and a channel 110 with an opening 112. The reservoir 108 and the channel 110 may be covered by a lid with a vent. The reservoir 108 defines a partially-enclosed volume (the cap-gap). The reservoir 108 may contain a composition that assists in retaining a liquid sample, such as water-swellable polymers or porous polymer matrices. Reagents may be deposited in the reservoir 108 and/or channel 110. The reagent composition may include one or more enzymes, binders, mediators, and the like. The reagents may include a chemical indicator for an optical system. The sensor strip 104 may have other configurations.

The sensor strip 104 may have a sample interface 114. In an electrochemical system, the sample interface 114 has conductors connected to at least two electrodes, such as a working electrode and a counter electrode. The electrodes may be disposed on a surface of the base 106 that forms the reservoir 108. The sample interface 114 may have other electrodes and/or conductors.

The sensor strip 104 preferably includes an encoding pattern 130 on the base 106. The encoding pattern 130 has at least two circuits, each forming a circuit pattern. The encoding pattern 130 may be a separate label affixed to the sensor strip 104 or elsewhere on the biosensor system 100, or the encoding pattern 130 may be integrally formed with the sensor strip 104. The encoding pattern 130 may be formed from the same material(s) used to form conductors, electrodes, and the like on the sensor strip 104. Other encoding patterns may be used. Each circuit pattern includes a unique or selected combination of electrically or physically interconnected positions on the encoding pattern. The circuit patterns may include all or part of the available positions on the encoding pattern.

The encoding pattern 130 may be located on the top, bottom, sides, or any other location on the sensor strip 104. The encoding pattern 130 may be on separate strips. For example, the encoding pattern 130 may be on a calibration strip for use with a set of measuring strips. The calibration strip may be another strip or may be part of or attached to a package containing the set of measuring strips. In addition, the calibration strip and the measuring strips each may have an encoding pattern. For example, the calibration strip may have a first encoding pattern that provides more general calibration information. Each measuring strip also may have a second encoding pattern that provides more specific calibration information. The encoding pattern 130 may be applied directly to a surface of sensor strip 104. The encoding pattern 130 may be formed using the same materials and similar techniques as used to create conductive measurement traces to reservoir 108, the conductors or electrodes on the sample interface 114, other components of the sensor strip 104, or the like. Other encoding patterns may be used.

The measurement device 102 includes electrical circuitry 116 connected to a sensor interface 118, a display 120, and a pattern read device 132. The sensor interface 118 and the pattern read device 132 may be the same component. The electrical circuitry 116 may include a processor 122 connected to a signal generator 124, an optional temperature sensor 126, and a storage medium 128. Electrical circuitry 116 may have other configurations including those with additional components. The sensor strip 104 may be configured for insertion into the measurement device 102 in only one orientation. The sensor strip 104 may be configured for insertion into the measurement device with an orientation that places the encoding pattern 130 in electrical or optical communication with the pattern read device 132 and with an orientation that places the sample interface in electrical and/or optical communication with the sensor interface 118.

The processor 122 provides a control signal to the pattern read device 132. The control signal may be an electrical signal such as potential, current, or the like. In optical systems, the control signal operates a first light source and a first detector in the pattern read device 132. Additional light sources and light detectors or an imaging device with pattern recognition may be used. The optical system senses the light reflected from the surface of the encoding pattern 130 or senses the light that passes through the encoding pattern 130. In electrical systems, the control signal may operate electrical contacts in the pattern read device 132 that are in electrical communication with contact areas on the encoding pattern 130. Electrical communication includes the transfer of signals between electrical contacts in the pattern read device 132 and contact areas in the encoding pattern 130. Electrical communication may be implemented wirelessly, such as by capacitive coupling, or through physical contact.

The signal generator 124 provides an electrical input signal to the sensor interface 118 in response to the processor 122. In optical systems, the electrical input signal operates a second light source and a second detector in the sensor interface 118. In electrochemical systems, the electrical input signal is transmitted by the sensor interface 118 to the sample interface 114 to apply the electrical input signal to the reservoir 108 and thus, to the sample of the biological fluid.

The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 124 also may record an output signal from the sensor interface 118 as a generator-recorder.

The storage medium 128 may be a magnetic, optical, or semiconductor memory, another computer readable storage device, or the like. The storage medium 128 may be a fixed memory device or a removable memory device such as a memory card.

The processor 122 may implement analyte analysis and data treatment using computer readable software code and data stored in the storage medium 128. The processor 122 may use calibration information from the encoding pattern 130 to calibrate the analyte analysis and data treatment.

The processor 122 may provide the control signal to the pattern read device 132 in response to: the presence of the sensor strip 104 at the sensor interface 118: the presence of the sensor strip 104 at the pattern read device 132: the application of a sample to the sensor strip 104: user input; or the like. The processor 122 may start the analyte analysis after obtaining the calibration information from the encoding pattern 130. To start the analysis, the processor 122 may direct the signal generator 124 to provide the electrical input signal to the sensor interface 118. The processor 122 may receive a sample temperature from the temperature sensor 126, if so equipped.

The processor 122 receives the calibration information from the pattern read device 132. The calibration information is responsive to the circuit patterns of the encoding pattern 130. The processor 122 also receives the output signal from the sensor interface 118. The output signal is generated in response to the redox reaction of the analyte in the sample. The output signal may be generated using an optical system, an electrochemical system, or the like. The processor 122 may use a correlation equation to determine the concentration of the analyte in the sample from one or more output signals. The correlation equation may be calibrated by the processor 122 in response to the calibration information from the encoding pattern 130. The results of the analyte analysis are output to the display 120 and may be stored in the storage medium 128.

Correlation equations relate the analyte concentrations with the output signals and may be represented graphically, mathematically, a combination thereof, or the like. The correlation equations may be represented by a program number assignment (PNA) table, another look-up table, or the like that is stored in the storage medium 128. Instructions regarding implementation of the analysis and use of the calibration information may be provided by the computer readable software code stored in the storage medium 128. The code may be object code or any other code describing or controlling the functionality described herein. The data from the analyte analysis may be subjected to one or more data treatments, including the determination of decay rates, K constants, slopes, intercepts, and/or sample temperature in the processor 122.

The sensor interface 118 is in electrical and/or optical communication with the sample interface 114. Electrical communication includes the transfer of input and/or output signals between contacts in the sensor interface 118 and conductors in the sample interface 114. Electrical communication may be implemented wirelessly or through physical contact. The sensor interface 118 transmits the electrical input signal from the signal generator 124 through the contacts to the connectors in the sample interface 114. The sensor interface 118 also transmits the output signal from the sample through the contacts to the processor 122 and/or the signal generator 124. Optical communication includes the transfer of light between an optical portal in the sample interface 114 and a detector in the sensor interface 118. Optical communication also includes the transfer of light between an optical portal in the sample interface 114 and a light source in the sensor interface 118.

Similarly, the pattern read device 132 is in electrical or optical communication with encoding pattern 130. Electrical communication includes the transfer of signals between the pattern read device 132 and the encoding pattern 130. Electrical communication may be implemented wirelessly or through physical contact. Optical communication includes the transfer of light from a light source in the pattern read device 132 to the encoding pattern 130. Optical communication also includes the transfer of light from the encoding pattern 130 to a detector in the pattern read device 132.

The display 120 may be analog or digital. The display 120 may be a LCD, LED, or vacuum fluorescent display adapted to displaying a numerical reading.

In use, a liquid sample for analysis is transferred into the reservoir 108 by introducing the liquid to the opening 112. The liquid sample flows through the channel 110 and into the reservoir 108, while expelling the previously contained air. The liquid sample chemically reacts with the reagents deposited in the channel 110 and/or the reservoir 108.

The processor 122 provides a control signal to the pattern read device 132. In optical systems, the pattern read device 132 operates the light source and detector in response to the control signal. In electrical systems, the pattern read device 132 operates an array of electrical contacts connected to the encoding pattern 130 in response to the control signal. The pattern read device 132 senses the circuit patterns on the encoding pattern 130 and provides calibration information in response to the circuit patterns. The processor 122 receives the calibration information from the encoding pattern 130.

The processor 122 also directs the signal generator 124 to provide an input signal to the sensor interface 118. In optical systems, the sensor interface 118 operates the detector and light source in response to the input signal. In electrochemical systems, the sensor interface 118 provides the input signal to the sample through the sample interface 114. The processor 122 receives the output signal generated in response to the redox reaction of the analyte in the sample. The processor 122 determines the analyte concentration of the sample using one or more correlation equations. The processor 122 may calibrate the correlation equations in response to the calibration information from the encoding pattern 130. The determined analyte concentration may be displayed and/or stored for future reference.

The measurement device 102 and the sensor strip 104 may implement an electrochemical analysis, an optical analysis, a combination thereof, or the like to determine one or more analyte concentrations in a sample of biological fluid. Optical analyses use the reaction of a chemical indicator with an analyte to determine the analyte concentration in the biological fluid. Electrochemical analyses use an oxidation/reduction or redox reaction of an analyte to determine the analyte concentration in the biological fluid.

An optical analysis generally measures the amount of light absorbed or generated by the reaction of a chemical indicator with the analyte. An enzyme may be included with the chemical indicator to enhance the reaction kinetics. The light from an optical system may be converted into an electrical signal such as current or potential.

In light-absorption optical analyses, the chemical indicator produces a reaction product that absorbs light. An incident excitation beam from a light source is directed toward the sample. The incident beam may be reflected back from or transmitted through the sample to a detector. The detector collects and measures the attenuated incident beam. The amount of light attenuated by the reaction product is an indication of the analyte concentration in the sample.

In light-generated optical analyses, the chemical detector fluoresces or emits light in response to the analyte during the redox reaction. A detector collects and measures the generated light. The amount of light produced by the chemical indicator is an indication of the analyte concentration in the sample.

During electrochemical analyses, an excitation signal is applied to the sample of the biological fluid. The excitation signal may be a potential or current and may be constant, variable, or a combination thereof. The excitation signal may be applied as a single pulse or in multiple pulses, sequences, or cycles. The analyte undergoes a redox reaction when the excitation signal is applied to the sample. An enzyme or similar species may be used to enhance the redox reaction of the analyte. A mediator may be used to maintain the oxidation state of the enzyme. The redox reaction generates an output signal that may be measured constantly or periodically during transient and/or steady-state output. Various electrochemical processes may be used such as amperometry, coulometry, voltammetry, gated amperometry, gated voltammetry, and the like.

The optical and electrochemical analyses use correlation equations to determine the analyte concentration of the biological fluid. Correlation equations are mathematical representations of the relationship between analyte concentrations and output signals such as light, current, or potential. The correlation equations may be linear, near linear, or curvilinear and may be described by a second order polynomial. From a correlation equation, an analyte concentration may be calculated for a particular output signal. A biosensor may have one or more correlation equation stored in a memory for use during the optical or electrochemical analysis. Different correlation equations may be needed, especially when different sensor strips are used or operating parameters such as the sample temperature change. Correlation equations may be implemented to manipulate the output signal for determination of the analyte concentration. Correlation equations also may be implemented as a program number assignment (PNA) table of the slope and intercept for the correlation equations, another look-up table, or the like for comparison with the output signals to determine the analyte concentration.

In FIG. 1, the measurement device 102 calibrates the correlation equations in response to calibration information from the sensor strip 104. The pattern read device 132 senses the circuit patterns of the encoding pattern 130, and provides a pattern signal to the processor 122 in response to the circuit patterns. The pattern signal may be an analog or digital electrical signal or the like. The processor 122 converts the pattern signal into the calibration information for use with the sensor strip 104. The processor 122 calibrates one or more of the correlation equations in response to the calibration information.

The calibration information may be any information used to calibrate correlation equations. Calibrate includes adjusting or modifying the concentration value or other result of a correlation equation. Calibrate includes selecting one or more correlation equations. For example, the calibration information may be identification information indicating the type of sensor strip, the analyte(s) or biological fluid associated with the sensor strip, the manufacturing lot of the sensor strip, the expiration date of the sensor strip, or the like. The processor 122 may select one or more correlation equations to use in response to the identification information. Calibrate also includes modifying one or more correlation equations. For example, the calibration information may provide or direct the use of an addition or subtraction to the slope and/or intercept of a correlation equation. Calibrate also includes providing one or more of the correlation equations. For example, the calibration information may include or direct the use of a slope and intercept for a correlation equation. Other calibration information may be used.

To obtain the calibration information, the pattern read device 132 senses the circuit patterns of at least two circuits formed by the encoding pattern 130. The pattern read device 132 may sense the circuit patterns optically or electrically. The encoding pattern 130 may be an electrically conductive material that is applied to the sensor strip 104 at a location accessible to the pattern read device 132. The electrically conductive materials may be carbon, silver, aluminum, palladium, copper, or the like. The encoding pattern 130 may be a non-conductive material or another material having sufficient contrast with the background material to be sensed optically.

The encoding pattern 130 of electrically conductive material may be divided into two or more separate circuits. The conductive material may be divided using laser ablation, scribing, photo etching, or like technique. By altering the cut path used to divide the conductive material into circuits, unique combinations of circuit patterns (interconnected contact areas) may be formed. The separate circuits also may be formed during the creation of the encoding pattern 130 on the sensor strip 104. The conductive material may have a rectangular or square shape, and may have other shapes such as triangular, circular, elliptical, a combination of shapes, or the like. The circuits may be formed by single or multiple orthogonal cuts, and may be formed by non-orthogonal cuts or a combination of orthogonal and non-orthogonal cuts. Orthogonal cuts are not required, but avoiding diagonal cuts may improve alignment of the circuits with the pattern read device 132.

Each circuit on the encoding pattern 130 may have one or more contact areas that are in electrical communication with the pattern read device 132. When each circuit has at least two contact areas, the detection of faulty contacts, open circuit conditions, and other errors from additional or missing material may be improved. The detection of these errors also may be improved when the encoding pattern 130 has two circuits that include all of the contact areas. The same number of circuits may be used on different strips to further improve the detection of these errors. When an error occurs, the measurement device 102 may notify the user and may reject and/or eject the sensor strip 104. Error checking may include determining whether a count of the circuit patterns matches the number of circuits on the encoding pattern 130. If the measurement device 102 cannot account for all the contact areas and all the circuit patterns on the encoding pattern 130, the measurement device 102 also may notify the user and may reject and/or eject the sensor strip 104.

FIGS. 2A-C depict various views of an encoding pattern 230 on a sensor strip 204. FIG. 2A depicts an array of electrical contacts 238 in electrical communication with the encoding pattern 230. FIG. 2B depicts the encoding pattern 230 prior to division into separate circuits. The encoding pattern 230 has contact areas A-F that are in electrical communication with the array of electrical contacts 238. FIG. 2C depicts the encoding pattern 230 after division into separate circuits. The encoding pattern 230 has been cut into a first circuit 234 and a second circuit 236. The first circuit 234 includes the contact areas A, C, E, and F that are in electrical communication with the electrical contacts A, C, E, and F of the array 238. The second circuit 236 includes the contact areas B and D that are in electrical communication with the electrical contacts B and D of the array 238. While a particular configuration is shown, the sensor strip 204, the encoding pattern 230, and the array 238 may have other configurations including those with additional components and encoding patterns divided into two or more circuits.

The array of electrical contacts 238 may be part of a pattern read device that uses the electrical contacts to sense the circuit patterns of the encoding pattern 230. The pattern read device may apply test signals to the circuits 234 and 236 through the array of electrical contacts 238 in response to a control signal. The test signals may be electrical signals such as current, potential, or the like. For example, the test signals may be limited to a current of less than about 50 microAmperes ($\mu$A). The test signals may be current limited in the range of about 1 $\mu$A through about 48 $\mu$A. The test signals may be current limited in the range of about 2 $\mu$A through about 15 $\mu$A. The test signals may be current limited in the range of about 2 $\mu$A through about 10 $\mu$A. The test signals may be current limited in the range of about 4 $\mu$A through about 8 $\mu$A. The current may be selected to provide short-circuit protection. The current may be selected to accommodate the resistance of the material used to produce the circuit patterns. Other currents or potentials may be used.

Referring to FIG. 1, a pattern read device selectively applies the test signals to sense the circuit patterns of circuits 234 and 236. The pattern read device drives selected electrical contacts in the array 238 to ground while applying test signals to other electrical contacts in the array 238. The test signals may be current limited and may have a different potential than other electrical contacts in the array 238. Other test signals may be used. "Ground" includes zero or near zero potential or current or the like. The pattern read device may individually drive one or more of the electrical contacts in the array 238 to ground. The pattern read device may apply the test signals in one or more steps or iterations, while changing the electrical contacts driven to ground in each step. After one or more steps, the pattern read device can determine the unique set of contacts contacting a particular circuit by determining what other contacts are forced low or to ground when a given contact is driven low or grounded. Thus, the pattern read device can determine the unique pattern of electrical contacts in the array 238 that are associated with each of the circuits 234 and 236. The unique patterns of the electrical contacts identify the circuit patterns of each circuit 234 and 236. The circuit patterns of circuits 234 and 236 may be used to provide calibration information for the optical or electrochemical analysis of an analyte in a biological fluid.

Alternatively, the pattern read device may selectively apply test signals that are the inverse of the test signals previously discussed. When using inverse test signals, the pattern read device may individually drive one or more electrical contacts to a potential other than ground while pulling the remaining electrical contacts to ground. A current limiting impedance may be used to pull electrical contacts to ground. Current sources may be used to drive electrical contacts to another potential. When read, only those electrical contacts connected to the driven electrical contacts are at the drive potential and the remaining contacts are grounded. The pattern read device may selectively apply other test signals.

Figure 3B:
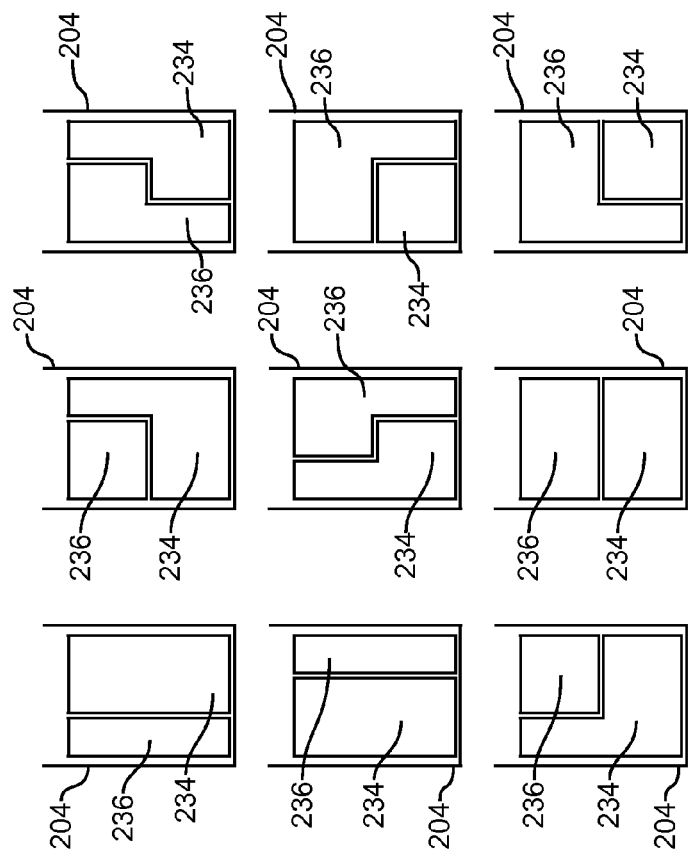
FIG. 3B depicts unique circuit patterns forming part of the encoding pattern in FIG. 3A.

FIGS. 3A-B depict circuit patterns that may be formed from the division of encoding pattern 230 on sensor strip 204 into circuits 234 and 236. FIG. 3A depicts an undivided encoding pattern 230 with contact areas X that are in electrical communication with the array of electrical contacts 238 in FIG. 2A. While the contact areas X are arranged in three columns and two rows, other configurations of the contact areas and array 238 may be used including those with fewer or additional contact areas and electrical contacts. The encoding pattern 230 may be divided into other circuit patterns.

FIG. 3B depicts circuit patterns that the circuits 234 and 236 may have. There are six contact areas arranged in three columns and two rows. The cut patterns are restricted to orthogonal cuts, although this is not required. In the case of orthogonal cuts, the two circuits created may be completed in one continuous cut. Thus, the circuits 234 and 236 may form nine unique circuit patterns when at least two electrical contacts from array 238 are in electrical communication with each circuit. The circuit patterns have various shapes, locations, and orientations on the encoding pattern 230. The circuit patterns each include a unique set of the contact areas, and thus a unique set of the electrical contacts in the array 238. The calibration information may be determined from the electrical contacts associated with particular circuit patterns.

Figures 4A, 4B:
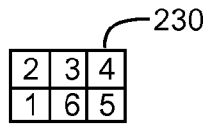
FIG. 4A depicts a numbering sequence of the contact areas on the encoding pattern in FIGS. 3A-B.
FIG. 4B depicts circuit patterns and respective digital representation of the circuits in FIG. 3B.

FIGS. 4A-B depict circuit patterns and respective digital representations of the circuits discussed in reference to FIGS. 3A-B. FIG. 4A depicts a numbering sequence of the contact areas on the encoding pattern 230, which corresponds to electrical contacts in array 238. The contact areas and corresponding electrical contacts are numbered 1 through 6. FIG. 4B depicts circuit patterns and respective digital representation of the circuits discussed in reference to FIG. 3B. The contact areas and corresponding electrical contacts of the first circuit 234 are identified by a "0" in each circuit pattern. The contact areas and corresponding electrical contacts of the second circuit 236 are identified by a "1" in each circuit pattern. The "0" and "1" labels were selected arbitrarily to identify the contact areas and corresponding electrical contacts belonging to a particular circuit. The labels may be interchanged. Other labels or number assignments may be used and may result in different digital representations.

The particular labels (0 or 1) for each contact area and corresponding electrical contact are listed sequentially according to the numbering sequence discussed in reference to FIG. 4A. While the numbering system decreases numerically from 6 through 1, the numbering sequence may increase numerically from 1 through 6. Other numbering sequences may be used. The sequence of the labels "0" or "1" provides a unique digital representation of each circuit pattern. Other digital representations of the circuit patterns may be used.

The digital representations of the circuit patterns may be used to provide the calibration information for analysis of an analyte in a biological fluid. The pattern read device may provide the digital representation of the circuit patterns through a pattern signal to a processor in a measurement device. The processor converts the digital representation into the calibration information.

FIG. 5 depicts a pattern read device 532 for sensing the circuit patterns of an encoding pattern 530 on a sensor strip 504. The encoding pattern 530 has a first circuit 534 and a second circuit 536. The pattern read device 532 has a decoder 550 and a code reader 552, each connected to a plurality of test circuits 554. Redundant circuitry of the pattern read device 532 is abbreviated for clarity. The decoder 550 may be a digital decoder or like device. The decoder 550 may be a select one of 'n' digital decoder. The decoder 550 may be a select one of 'n' digital decoder, where n=6. Other digital decoders may be used. The code reader 552 may be a digital input port or like device. Each test circuit 554 is connected to a separate electrical contact A-F in an array of electrical contacts 538. The electrical contacts A-F may have electrical communication with contact areas on the first circuit 534 and the second circuit 536 of the encoding pattern 530. While particular circuit patterns are shown, the first circuit 534 and the second circuit 536 may have other circuit patterns including those using different contact areas and corresponding electrical contacts. While a particular configuration is shown for the pattern read device, other configurations may be used including those with additional components. Other pattern read devices may be used.

In use, a processor in a measurement device sends a control signal to the decoder 550 in the pattern read device 532. The processor also activates a pull-up voltage in each of the test circuits 554. The pull-up voltage may cause each test circuit 554 to apply a test signal or current to the electrical contacts A-F in the array 538. The test signals may be limited to a current of less than about 50 µA. The test signals may be current limited in the range of about 1 µA through about 48 µA. The test signals may be current limited in the range of about 2 µA through about 15 µA. The test signals may be current limited in the range of about 2 µA through about 10 µA. The test signals may be a current in the range of about 4 µA through about 8 µA. Other currents may be used. The processor also activates the code reader 552 to sense the test signals applied to each electrical contact in the array 538.

The pattern read device 532 selectively applies the test signals to determine the circuit patterns of circuits 534 and 536 on the encoding pattern 530. The test circuits 554 apply the test signals to the electrical contacts A-F of array 538. The code reader 552 senses the test signals. To sense the circuit patterns, the pattern read device 532 individually drives one or more electrical contacts in the array 538 to ground while applying pull-up voltage test signals to the other electrical contacts in the array 538. The decoder 550 applies an operating signal to one or more of test circuits 554 in response to the control signal. The operating signal drives the respective test circuit and corresponding electrical contact to ground.

The circuits 534 and 536 on the encoding pattern 530 create electrical connections between the electrical contacts A-F of the array 538 when the electrical contacts are in electrical communication with the circuits. When a particular electrical contact on a circuit is driven to ground, the test signals of the other electrical contacts on the circuit are reduced or driven to ground. The code reader 552 uses the reduced or grounded test signals to identify the electrical contacts associated with the particular electrical contact that was driven to ground. The electrical contacts associated with the grounded electrical contact may be used to identify the circuit pattern. The code reader 552 generates a pattern signal that identifies the circuit patterns on the encoding pattern 530. The pattern signal may be a digital representation of the circuit patterns. The processor receives the pattern signal from the code reader 552. The pattern signal may include calibration information. The processor may convert the pattern signal into calibration information or use the pattern signal to locate calibration information in a storage medium. The processor uses calibration information to calibrate one or more correlation equations used to determine the analyte concentration in the biological fluid.

The pattern read device may apply the test signals in one or more steps or iterations. Different electrical contacts are driven to ground in each step. After one or more steps, the pattern read device may determine the unique set of electrical contacts corresponding to a particular circuit by determining which electrical contacts have reduced or grounded test signals in response to the electrical contract driven to ground. Thus, the pattern read device can determine the unique set of electrical contacts in the array 538 that are associated with each of the circuits 534 and 536 on the encoding pattern 530. The unique set of electrical contacts identifies the circuit patterns of each circuit 534 and 536. The circuit patterns of circuits 534 and 536 may be used to provide calibration information for the optical or electrochemical analysis of an analyte in a biological fluid. While particular sets of electrical contacts are shown to identify the circuit patterns, other sets of electrical contacts may be used to show other circuit patterns for circuits 534 and 536.

For example, electrical contacts A, C, E, and F correspond to the circuit pattern of the first circuit 534. Electrical contacts B and D correspond to the circuit pattern of the second circuit

536. To sense which electrical contacts correspond to particular circuit patterns, the pattern read device 532 applies test signals to the electrical contacts and individually drives one or more of the electrical contacts to ground in one or more steps or iterations. The pattern read device can determine the electrical contacts corresponding to a particular circuit pattern by determining which electrical contacts have reduced or grounded test signals in response to the electrical contract driven to ground. The circuit patterns may be identified after the first step. One or more additional steps may be done to confirm the results. Examples are presented for clarity and illustrative purposes and not to limit the invention.

In a first step, a first test signal from a first test circuit to electrical contact A is driven to ground while test signals are applied to the other electrical contacts. When electrical contact A is grounded, the test signals of the electrical contacts C, E, and F are reduced or grounded since these electrical contacts correspond to the first circuit 534. However, the test signals of electrical contacts B and D are not reduced or grounded and remain substantially the same since these electrical contacts correspond to the second circuit 536 and are not electrically connected to the first circuit 534.

In a second step, a second test signal from a second test circuit to electrical contact E is driven to ground while test signals are applied to the other electrical contacts. When electrical contact E is grounded, the test signals of electrical contacts A, C, and F are reduced or grounded since these electrical contacts correspond to the first circuit 534. However, the test signals of electrical contacts B and D are not reduced or grounded and remain substantially the same since these electrical contacts correspond to the second circuit 536.

In a third step, a third test signal from a third test circuit to electrical contact B is driven to ground while test signals are applied to the other electrical contacts. When electrical contact B is grounded, the test signal of electrical contact D is reduced or grounded since this electrical contact corresponds to the second circuit 536. However, the test signals of electrical contacts A, C, E, and F are not reduced or grounded and remain substantially the same since these electrical contacts correspond to the first circuit 534. The number of read steps may be reduced or minimized by reviewing the results of prior read steps and grounding a pin that has not been accounted for in the circuits identified by the prior read steps.

FIGS. 6-10 depict various circuit patterns from the division of encoding patterns into two circuits. The encoding patterns may be divided into more and/or other circuits. While the contact areas and the corresponding electrical contacts in the array have a particular configuration, other configurations of the contact areas and electrical contacts may be used including those with fewer or additional components. The maximum number of contact areas may be constrained by the size of the sensor strip and other design considerations. The circuit patterns have various shapes, locations, and orientations on the encoding patterns. Other circuit patterns may be used. The circuit patterns each include a unique set of the contact areas, and thus a unique set of the electrical contacts in the array. The calibration information may be determined from the electrical contacts associated with a particular circuit pattern. Each contact area may have a "0" or "1" label, which is arbitrarily selected to identify the contact areas and corresponding electrical contacts belonging to a particular circuit. The labels may be interchanged. Other labels or number assignments may be used and may result in different digital representations. The sequence of the labels "0" or "1" may be used to provide a unique digital representation of each circuit pattern. Other digital representations of the circuit patterns may be used. The digital representations of the circuit patterns may be used to provide the calibration information for analysis of an analyte in a biological fluid.

Figure 6A:
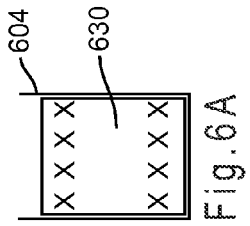
FIG. 6A depicts another undivided encoding pattern with contact areas X in electrical communication with an array of electrical contacts.
Figure 6B:
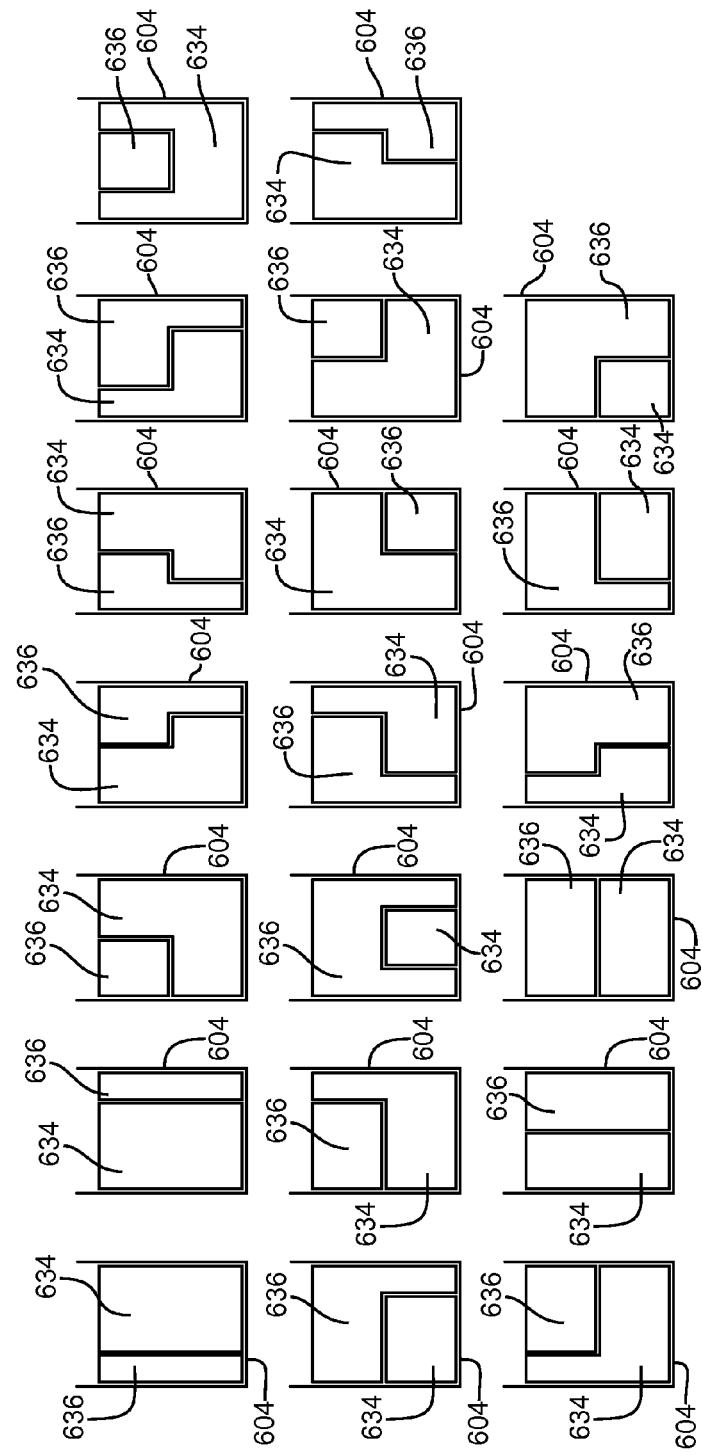
FIG. 6B depicts unique circuit patterns that may form the encoding pattern of FIG. 6A.

FIGS. 6A-B depict various circuit patterns from the division of encoding pattern 630 disposed on a sensor strip 604 into circuits 634 and 636. FIG. 6A depicts an undivided encoding pattern 630 with contact areas X that are in electrical communication with an array of electrical contacts. The contact areas X are arranged in four columns and two rows. FIG. 6B depicts different circuit patterns that the circuits 634 and 636 may have. Since the array has four columns and two rows, the circuits 634 and 636 may form 20 unique circuit patterns when at least two electrical contacts from an array are in electrical communication with each circuit. The depicted circuit patterns are restricted because only orthogonal cuts are used. Additional circuit patterns of interconnection are possible if non-orthogonal cuts or a combination of orthogonal and non-orthogonal cuts are used, as well as if more than two circuits are created.

Figures 7A, 7B:
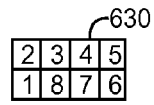
FIG. 7A depicts a numbering sequence of the contact areas on the encoding pattern in FIGS. 6A-B
FIG. 7B depicts circuit patterns and respective digital representations of the circuits of FIG. 6B.

FIGS. 7A-B depict circuit patterns and respective digital representations of the circuits discussed in reference to FIGS. 6A-B. FIG. 7A depicts a numbering sequence of the contact areas on the encoding pattern 630, which also corresponds to electrical contacts in the array. The contact areas and corresponding electrical contacts are numbered 1 through 8. FIG. 7B depicts circuit patterns and respective digital representations of the circuits discussed in reference to FIG. 6B. The contact areas and corresponding electrical contacts of the first circuit 634 and the second circuit 636 are identified, respectively, by a "0" or a "1" in each circuit pattern. The particular labels (0 or 1) for each contact area and corresponding electrical contact are listed sequentially according to the numbering sequence discussed in reference to FIG. 7A. The numbering system may decrease numerically from 8 through 1 or may increase numerically from 1 through 8. Other numbering sequences may be used. The sequences of "0's" and "1's" may provide unique digital representations of the circuit patterns. The digital representations may be assigned assuming that the circuit including bit 8 always represents a "0". The inverse of this coding could also be used and the coding could be keyed to another bit position.

FIGS. 8A-B depict various circuit patterns from the division of another encoding pattern 830 on a sensor strip 804 into circuits 834 and 836. FIG. 8A depicts an undivided encoding pattern 830 with contact areas X that are in electrical communication with an array of electrical contacts. The contact areas X are arranged in three columns and three rows. FIG. 8B depicts unique circuit patterns the circuits 834 and 836 may have. Since the array has three columns and three rows, the circuits 834 and 836 may form 44 unique circuit patterns when at least two electrical contacts from an array are in electrical communication with each circuit. The circuit patterns are those with a restriction of orthogonal cuts imposed. Additional circuit patterns of interconnection are possible if this restriction is not imposed.

Figures 9A, 9B:
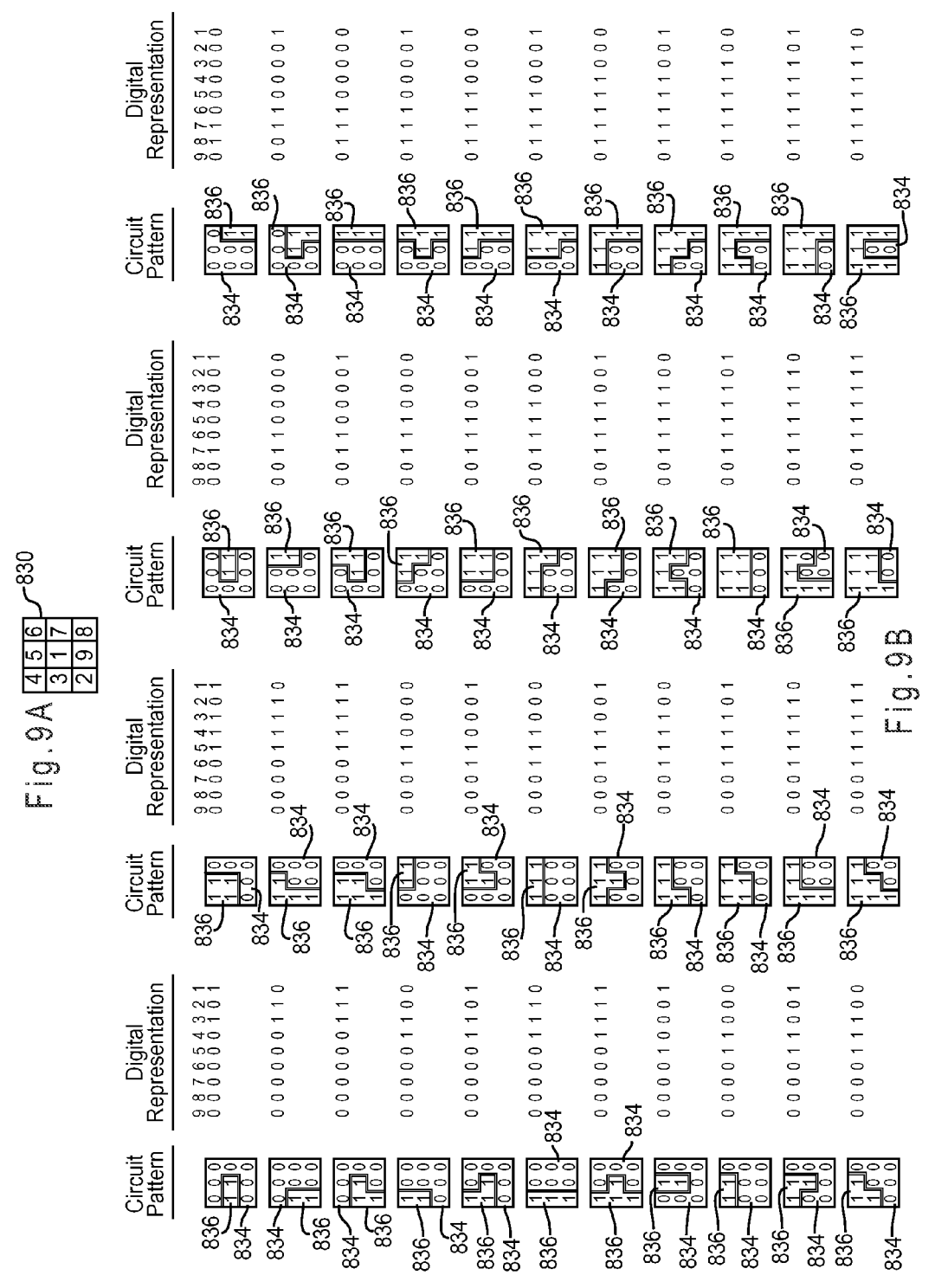

FIGS. 9A-B depict circuit patterns and respective digital representations of the circuits discussed in reference to FIGS. 8A-B. FIG. 9A depicts a numbering sequence of the contact areas on the encoding pattern 830, which also correspond to electrical contacts in the array. The contact areas and corresponding electrical contacts are numbered 1 through 9. FIG. 9B depicts circuit patterns and respective digital representations of the circuits discussed in reference to FIG. 8B. The contact areas and corresponding electrical contacts of the first circuit 834 and the second circuit 836 are identified, respectively, by a "0" or a "1" in each circuit pattern. The particular labels (0 or 1) for each contact area and corresponding electrical contact are listed sequentially according to the numbering sequence discussed in reference to FIG. 9A. The numbering system may decrease numerically from 9 through 1 or may increase numerically from 1 through 9. Other numbering sequences may be used. The sequence of the labels "0" or "1" provide a unique digital representation of each circuit pattern. The digital representations may be assigned assuming that the circuit including bit 9 always represents a "0". The inverse of this coding could also be used and the coding could be keyed to another bit position.

Figures 10A, 10B:
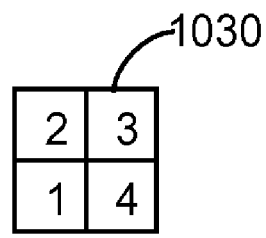
FIG. 10A depicts a numbering sequence of the contact areas on another encoding pattern.
FIG. 10B depicts circuit patterns and the respective digital representations of the circuits.

FIGS. 10A-B depict circuit patterns and respective digital representations from the division of another encoding pattern 1030 on a sensor strip (not shown) into circuits 1034 and 1036. FIG. 10A depicts a numbering sequence of the contact areas on the encoding pattern 1030, which also corresponds to electrical contacts in an array. The contact areas and corresponding electrical contacts are numbered 1 through 4. The contact areas are arranged in two columns and two rows. The circuit patterns are those with a restriction of orthogonal cuts imposed. Additional circuit patterns of interconnection are possible if this restriction is not imposed.

FIG. 10B depicts circuit patterns and respective digital representations that the circuits 1034 and 1036 may have. Since the array has two columns and two rows, the circuits 1034 and 1036 may form two unique circuit patterns when at least two electrical contacts from an array are in electrical communication with each circuit. The contact areas and corresponding electrical contacts of the first circuit 1034 and the second circuit 1036 are identified, respectively, by a "0" or a "1" in each circuit pattern. The particular labels (0 or 1) for each contact area and corresponding electrical contact are listed sequentially according to the numbering sequence discussed in reference to FIG. 10A. The numbering system may decrease numerically from 4 through 1 or may increase numerically from 1 through 4. Other numbering sequences may be used. The sequences of the labels "0" or "1" may provide unique digital representations of circuit patterns. The digital representations may be assigned assuming that the circuit including bit 4 always represents a "0". The inverse of this coding could also be used and the coding could be keyed to another bit position.

Encoding patterns may be divided into more than two circuits. Encoding patterns on different sensor strips each may be divided to have the same number of circuits or may be divided to have a different numbers of circuits. When an encoding pattern has two or more circuits, one or more of the circuits may be an isolated circuit. An isolated circuit may have only one contact area that is in electrical communication with only one electrical contact in the array. Other isolated circuits may be used. The isolated circuit may increase the number of unique circuit patterns that may be used to provide calibration information for analysis of an analyte in a biological fluid. When the number of isolated contacts is a fixed number, contact failures may be detected by verifying that the number of isolated contacts detected matches the designated fixed quantity of isolated circuit contacts. Unique circuit patterns may be formed when at least one circuit includes multiple contact positions.

Figure 11A:
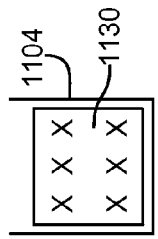
FIG. 11A depicts another undivided encoding pattern.
Figure 11B:
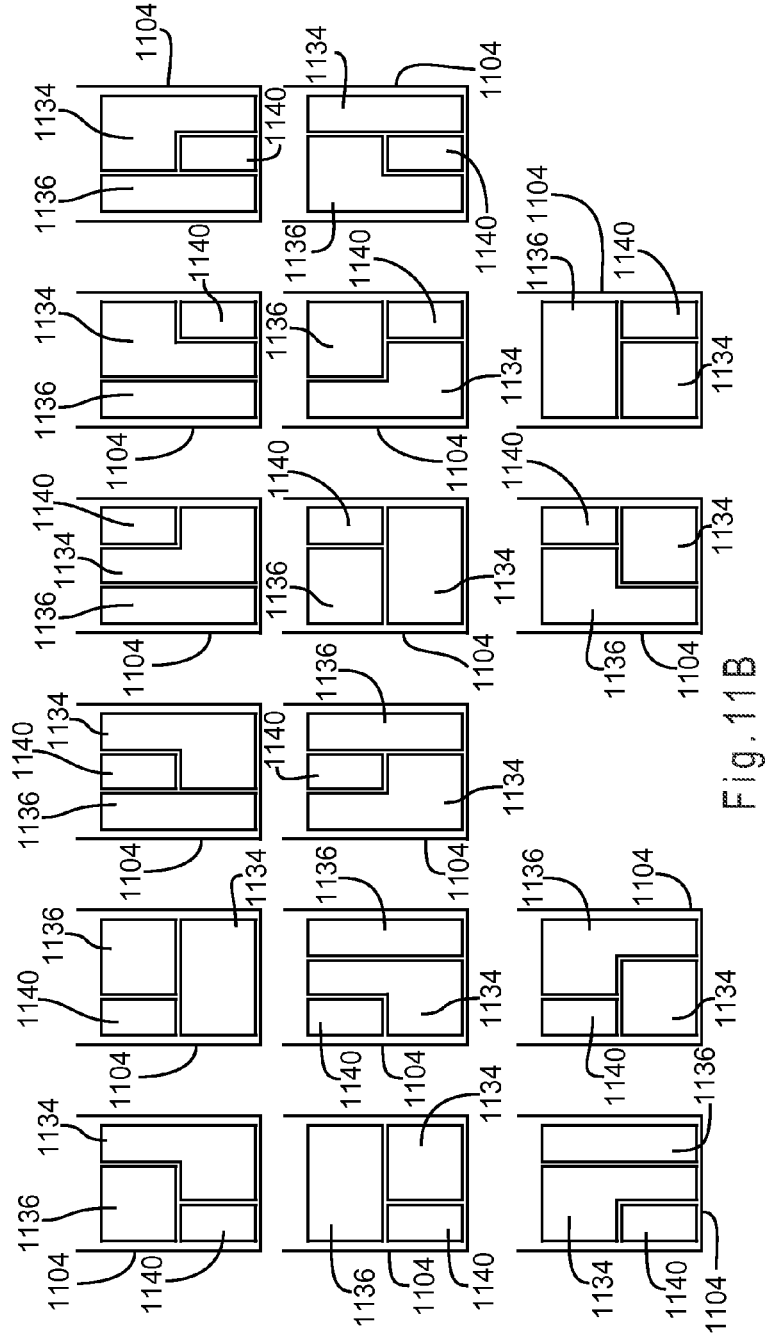
FIG. 11B depicts unique circuit patterns for a first circuit, a second circuit, and an isolated circuit for the encoding pattern of FIG. 11A.

FIGS. 11A-B depict various circuit patterns from the division of an encoding pattern 1130 into a first circuit 1134, a second circuit 1136, and an isolated circuit 1140 on a sensor strip 1104. FIG. 11A depicts an undivided encoding pattern 1130 with contact areas X that are in electrical communication with an array of electrical contacts. While the contact areas X are arranged in three columns and two rows, other configurations of the contact areas and the array may be used.

FIG. 11B depicts unique circuit patterns that the first circuit 1134, the second circuit 1136, and the isolated circuit 1140 may have. The circuits 1134, 1136, and 1140 may form 16 unique circuit patterns when at least two electrical contacts are in electrical communication with each of the first circuit 1134 and the second circuit 1136, and when one electrical contact is in electrical communication with the isolated circuit 1140. The circuit patterns have various shapes, locations, and orientations. The circuit patterns of the first circuit 1134 and the second circuit 1136 each include a unique set of the contact areas, and thus a unique set of the electrical contacts. The circuit pattern of the isolated circuit 1140 includes a particular contact area, and thus a particular electrical contact. The calibration information may be determined from the electrical contacts associated with the circuit patterns.

The multiple circuits produced by the pattern on the sensor strip allows for inherent error checking of the coding information. The error checking may be obtained by enforcing rules regarding the total number circuits and the total number of isolated circuits. By enforcing such rules, the measuring device may detect faulty patterns or readings and thus may reject a sensor strip before an erroneous test result is reported or after the error is detected. To allow for error detection (particularly faulty contacts or shorts), the number of isolated contacts may be a predefined fixed number. Thus, if more or less than the predefined number of isolated contacts are detected, a contact fault or short circuit must have occurred and the decoded patterns may be treated as invalid. The total number of circuits, both multiple contact and single contact, likewise may be a predefined fixed number. Similarly, if more or less than the predefined number of circuits is detected, a fault must have occurred and the decoded patterns should be treated as invalid.

Figure 12A:
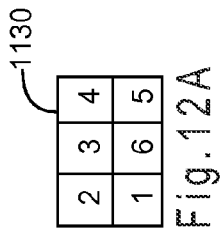
FIG. 12A depicts a numbering sequence of the contact areas on the encoding patterns of FIGS. 11A-B.
Figure 12B:
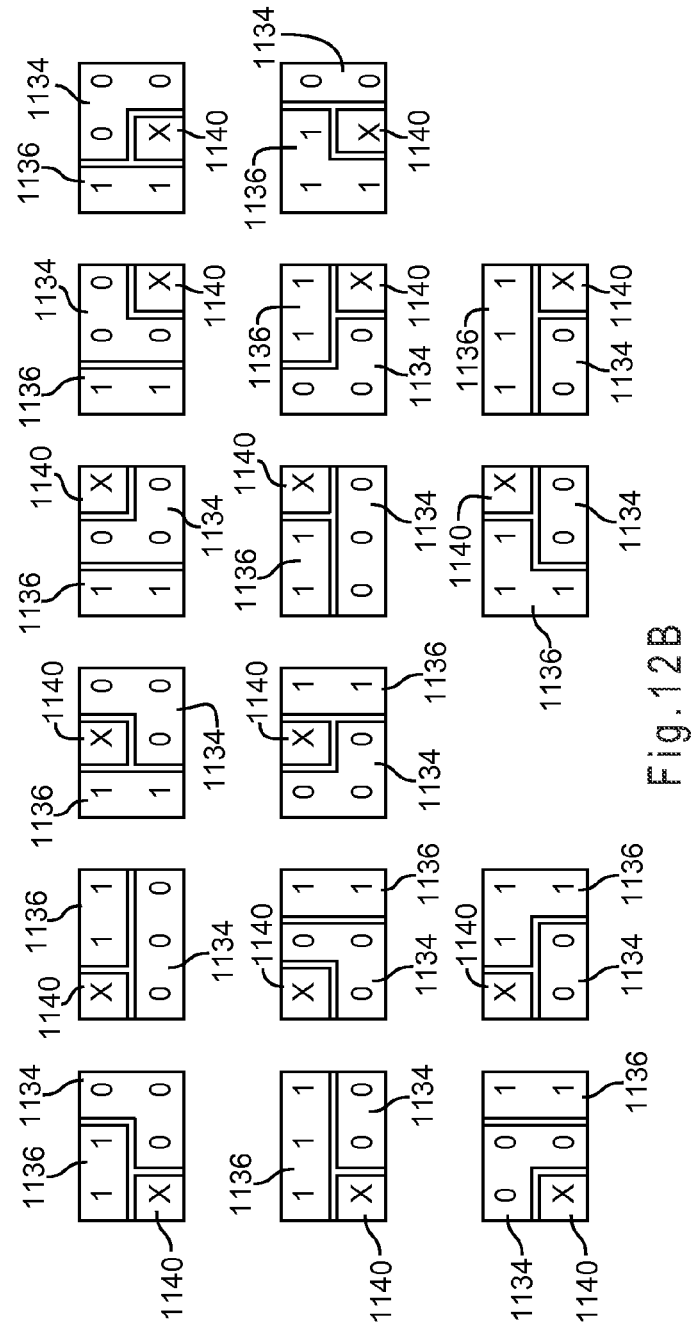
FIG. 12B depicts other views of the circuit patterns discussed in reference to FIG. 11B.

FIGS. 12A-B depict other views of the circuit patterns discussed in reference to FIGS. 11A-B. FIG. 12A depicts a numbering sequence of the contact areas on the encoding pattern 1130, which corresponds to electrical contacts. The contact areas and corresponding electrical contacts are numbered 1 through 6. FIG. 12B depicts another view of the circuit patterns discussed in reference to FIG. 11B. The contact areas and corresponding electrical contacts of the first circuit 1134 are identified by a "0" in each circuit pattern. The contact areas and corresponding electrical contacts of the second circuit 1136 are identified by a "1" in each circuit pattern. The contact area and corresponding electrical contact of the isolated circuit 1140 is identified by an "X" in the circuit pattern. The labels (0, 1, and X) are used to identify the particular circuit to which the contact areas and corresponding electrical contacts belong. The labels may be interchanged. Other labels may be used. The particular labels for each contact area and corresponding electrical contact are listed sequentially according to the numbering sequence discussed in reference to FIG. 12A. Other numbering sequences may be used. The sequence of the labels (0, 1, and X) may provide a unique digital representation of each circuit pattern. The digital representations of the circuit patterns may be used to provide the calibration information for analysis of an analyte in a biological fluid. The digital representations may be assigned assuming that the circuit including bit 6 always represents a "0" unless it is an isolated contact. If bit 6 is an isolated contact, then the circuit including bit 5 always represents a "0". The inverse of this coding could also be used and the coding could be keyed to other bit positions.

Figure 13:
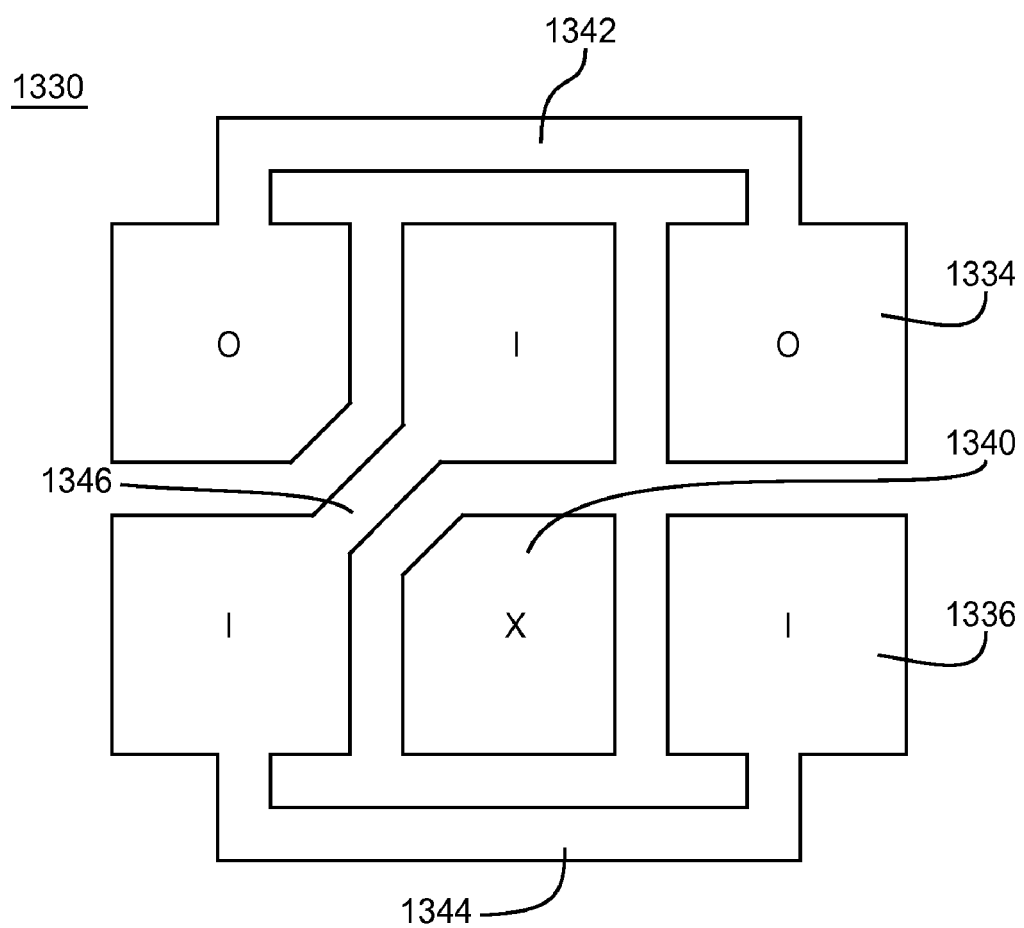
FIG. 13 depicts an encoding pattern divided into a first circuit, a second circuit, and an isolated circuit.

FIG. 13 depicts an encoding pattern 1330 divided into a first circuit 1334, a second circuit 1336, and an isolated circuit 1340. The contact areas of the first circuit 1334 and the second circuit 1336 are not adjacent and are connected using conductive traces, which provide an electrical connection between the non-adjacent locations on the encoding pattern

1330. The contact areas of the first circuit 1334 are identified by a "0" and are connected by a first conductive trace 1342. The contact areas of the second circuit 1336 are identified by a "1" and are connected by a second conductive trace 1344 and a diagonal conductive trace 1346. The contact area of the isolated circuit 1340 is identified by an "X" in the circuit pattern. The non-adjacent contact areas of the first circuit 1334 and the second circuit 1336 may increase the number of unique circuit patterns that may be used to provide calibration information for analysis of an analyte in a biological fluid.

Figure 14A:
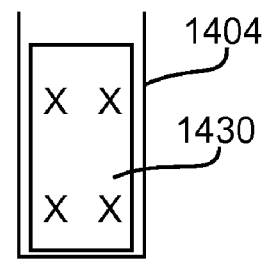
FIG. 14A depicts an additional undivided encoding pattern with contact areas X in electrical communication with an array of electrical contacts.
Figure 14B:
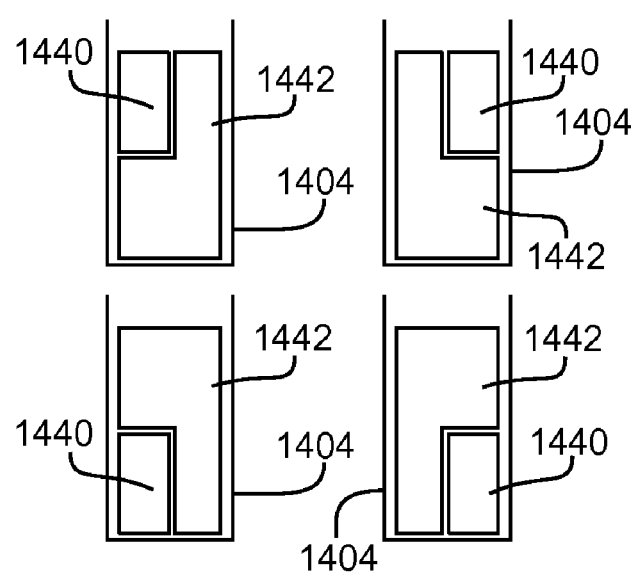
FIG. 14B depicts unique circuit patterns a multiple-contact and a single-contact circuit may have on the encoding pattern in FIG. 14A.

FIGS. 14A-B depict various circuit patterns from the division of an encoding pattern 1430 into an isolated or single-contact circuit 1440 and a multiple-contact circuit 1442 on a sensor strip 1404. FIG. 14A depicts an undivided encoding pattern 1430 with contact areas X that are in electrical communication with an array of electrical contacts. While the contact areas X are arranged in two columns and two rows, other configurations of the contact areas and array may be used.

FIG. 14B depicts unique circuit patterns that the single-contact circuit 1440 and the multiple-contact circuit 1442 may have. The circuits 1440 and 1442 may form four unique circuit patterns when three electrical contacts are in electrical communication with the multiple-contact circuit 1442, and when one electrical contact is in electrical communication with the single-contact circuit 1440. The circuit patterns may have various shapes, locations, and orientations. The circuit patterns of the single-contact circuit 1440 and the multiple-contact circuit 1442 each include a unique set of the contact areas, and thus a unique set of the electrical contacts. The circuit pattern of the single-contact circuit 1440 includes a particular contact area, and thus a particular electrical contact. The calibration information may be determined from the electrical contacts associated with the circuit patterns.

To provide error detection (particularly faulty contacts or shorts), if more or less than one single-contact circuit is detected, a contact fault or short circuit must have occurred and the decoded patterns may be treated as invalid. Similarly, if more or less than two circuits are detected, a fault must have occurred and the decoded patterns should be treated as invalid.

Additionally, unique circuit patterns may be formed when at least one circuit involves multiple contacts even when the remaining circuit(s) is an isolated or single-contact circuit. The total number of contacts and the configuration of the electrical contacts may be selected to provide a better or optimum balance of multi-contact circuits and single-contact circuits. When only four electrical contacts are used, one three-contact circuit and one single-contact circuit may better preserve error checking enabling verification that there are two circuits and only one isolated contact present.

Figure 15A:
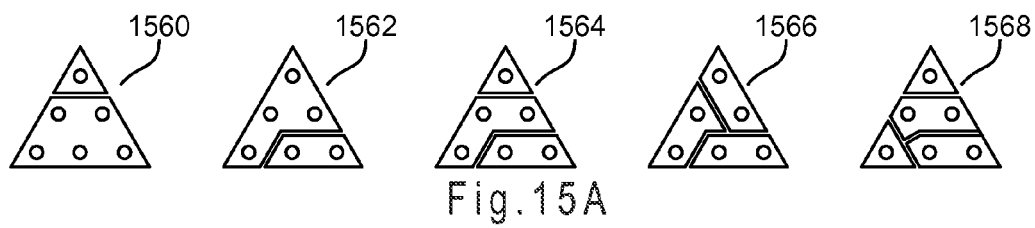
FIG. 15A depicts various triangular encoding patterns.
Figure 15B:
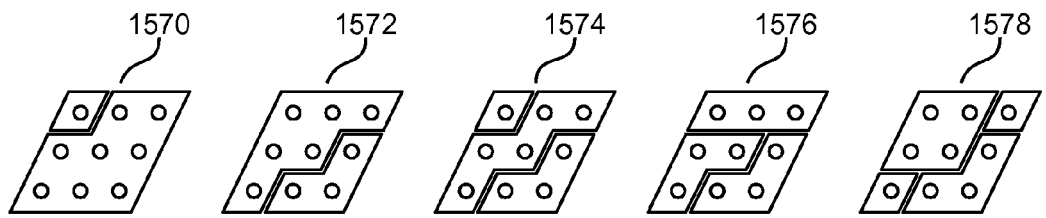
FIG. 15B depicts various rhomboidal encoding patterns.
Figure 15C:
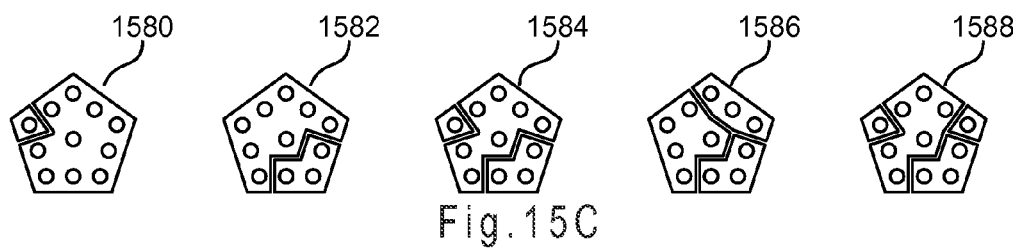
FIG. 15C depicts various pentagonal encoding patterns.
Figure 15D:
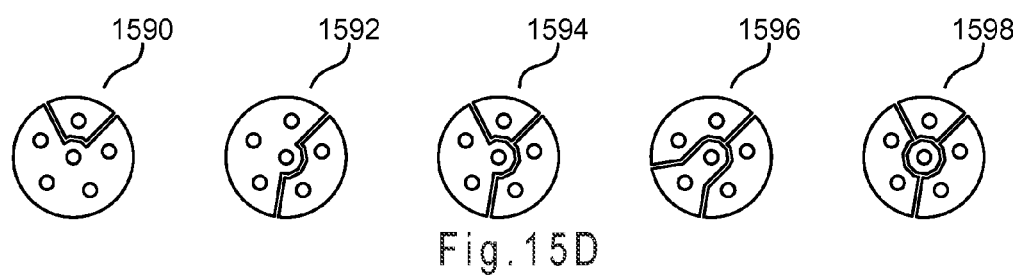
FIG. 15D depicts various circular encoding patterns.

FIGS. 15A-D depict various encoding patterns with non-rectangular arrays of patterns and contacts. FIG. 15A depicts various triangular encoding patterns 1560-1568. FIG. 15B depicts various rhomboidal encoding patterns 1570-1578. FIG. 15C depicts various pentagonal encoding patterns 1580-1588. FIG. 15D depicts various circular encoding patterns 1590-1598. The encoding patterns are divided into two, three, or four circuit patterns. Some circuit patterns have two or more contacts. Other circuit patterns are isolated or have a single-contact. A measuring device may not directly sense an isolated or single-contact circuit pattern since the measuring device takes at least two contacts to measure continuity. The encoding rules may be selected for a particular encoding pattern to specify the number of isolated circuit patterns allowed. Other non-rectangular arrays of patterns and contacts may be used.

Figure 16A:
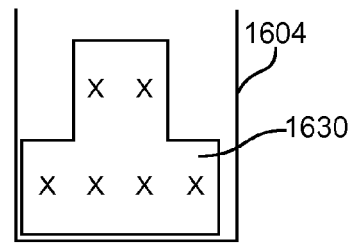
FIG. 16A depicts an undivided encoding pattern having a irregular shape.
Figure 16B:
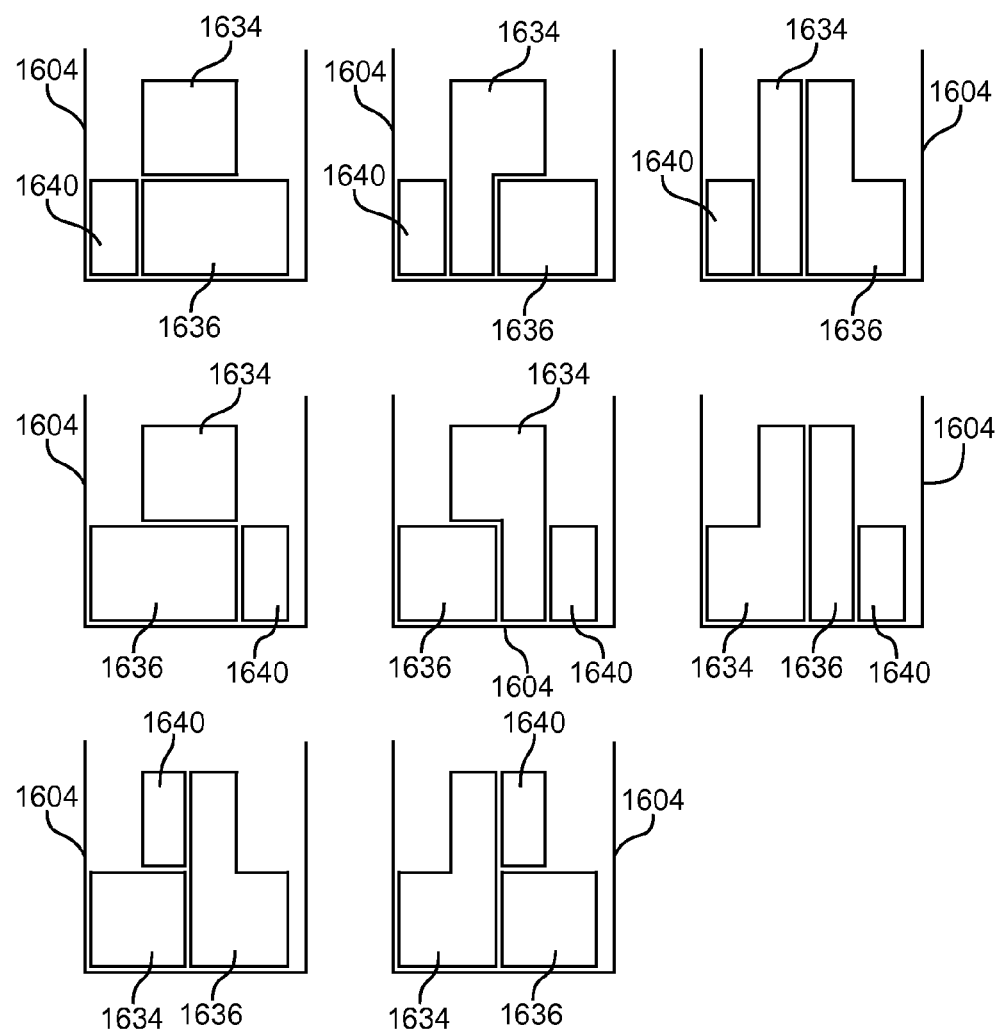
FIG. 16B depicts unique circuit patterns a first circuit, a second circuit, and a third circuit for the encoding pattern of FIG. 16A.

FIGS. 16A-B depict various circuit patterns from the division of an encoding pattern 1630 with an irregular shape into a first circuit 1634, a second circuit 1636, and a third circuit 1640 on a sensor strip 1604. FIG. 16A depicts an undivided encoding pattern 1630 with contact areas X that are in electrical communication with an array of electrical contacts. FIG. 16B depicts unique circuit patterns that the first circuit 1634, the second circuit 1636, and the third circuit 1640 may have. The irregular shape may be used if space must be kept clear for sensor contacts (not shown). When three circuit patterns are used, one of the circuit patterns may be an isolated or single-contact circuit. Other irregular shapes may be used. Other configurations of the contact areas and the array may be used.

Figure 17:
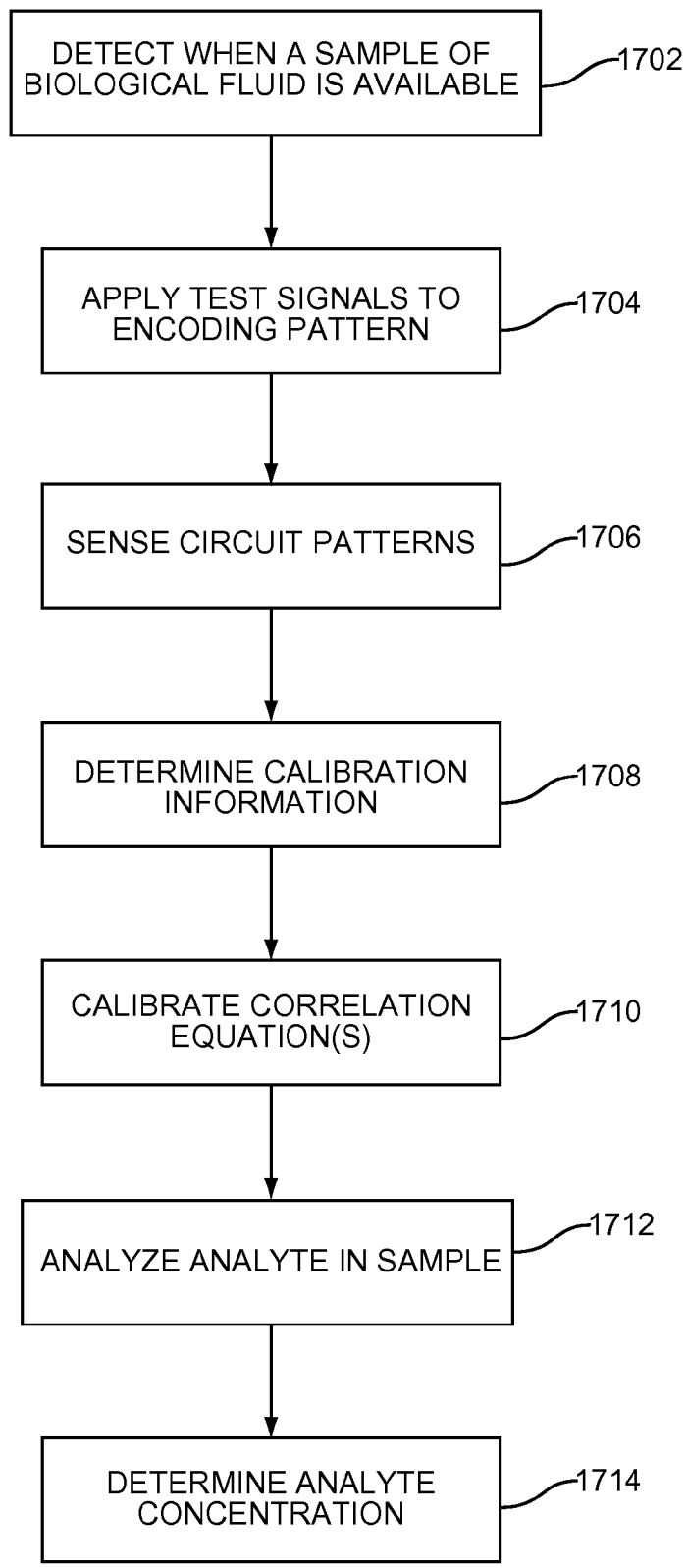
FIG. 17 represents a method for calibrating a biosensor.

FIG. 17 represents a method for calibrating an analysis of an analyte in a biological fluid. In 1702, a sample of a biological fluid is detected when available for analysis. In 1704, test signals are applied to an encoding pattern. In 1706, circuit patterns on the encoding pattern are sensed. In 1708, calibration information is determined in response to the circuit patterns. In 1710, one or more correlation equations are calibrated in response to the calibration information. In 1712, the analyte in the sample is analyzed. In 1714, the analyte concentration of the biological fluid is determined using one or more calibrated correlation equations.

In 1702, a biosensor detects when a sample of biological fluid is available for analysis. The biosensor may sense when a sensor strip is placed in a measuring device. The biosensor may sense when electrical contacts in the measuring device connect with electrical conductors in the sensor strip. The biosensor may apply one or more signals to the working, counter, and/or other electrodes to detect when a sample connects with the electrodes. The biosensor may use other methods and devices to detect when a sample is available for analysis.

In 1704, the biosensor applies test signals from a measurement device to an encoding pattern on a sensor strip, sensor strip package, or the like. The test signals may be generated optically or electrically. The biosensor selectively applies the test signals to the encoding pattern as previously discussed. The biosensor may apply the test signals in one or more steps or iterations.

In 1706, the biosensor senses the circuit patterns of at least two circuits on the encoding strip. The circuit patterns may be sensed optically or electrically as previously discussed. A pattern signal may be used to identify the circuit patterns on the encoding pattern.

In 1708, the biosensor determines the calibration information in response to the circuit patterns. The calibration information may be any information used to adjust correlation equations for electrochemical and/or optical analyses. Calibration information may be identification information indicating the type of sensor strip, the analyte(s) or biological fluid associated with the sensor strip, the manufacturing lot of the sensor strip, or the like. Calibration information may provide an addition or subtraction to the slope and/or intercept of a correlation equation. Calibration information may include or direct the use of a slope and intercept for a correlation equation. Other calibration information may be used. The calibration information may reference parameters and adjustments stored in a memory device in the biosensor. A processor may select stored reference parameters and adjustments in response to a pattern or other signal indicating the circuit patterns on the encoding pattern.

In 1710, the biosensor calibrates one or more correlation equations in response to the calibration information. Correlation equations may be used to determine the analyte concentration in optical and/or electrochemical analyzes. Correlation equations are mathematical representations of the relationship between analyte concentrations and output signals such as light, current, or potential as previously discussed. Calibrate includes adjusting or modifying the concentration value or other result of a correlation equation. Calibrate may include selecting one or more correlation equations in response to identification information indicating the type of sensor strip, the analyte(s) or biological fluid associated with the sensor strip, the manufacturing lot of the sensor strip, the expiration date of the sensor strip, or the like. Calibrate may include modifying one or more correlation equations with an addition or subtraction to the slope and/or intercept of the correlation equation. Calibrate may include providing one or more of the correlation equations.

In 1712, the biosensor analyzes the analyte in the sample using an electrochemical analysis, an optical analysis, a combination thereof, or the like. In an electrochemical analysis, the analyte undergoes a redox reaction when an excitation signal is applied to the sample. The redox reaction generates an output signal that may be measured and correlated to the analyte concentration. Various electrochemical processes may be used such as amperometry, coulometry, voltammetry, gated amperometry, gated voltammetry, or the like as previously discussed. An optical analysis measures the amount of light absorbed or generated by the reaction of a chemical indicator with the analyte. The amount of light may be measured and correlated to the analyte concentration. The optical analysis may be light-absorption or light-generated as previously discussed.

In 1714, the biosensor determines the analyte concentration in the sample of the biological fluid. The biosensor may use one or more of the calibrated correlation equations to determine the analyte concentration of the sample. The biosensor may use the calibrated analyte value or other result to determine the analyte concentration of the sample.

Figure 18:
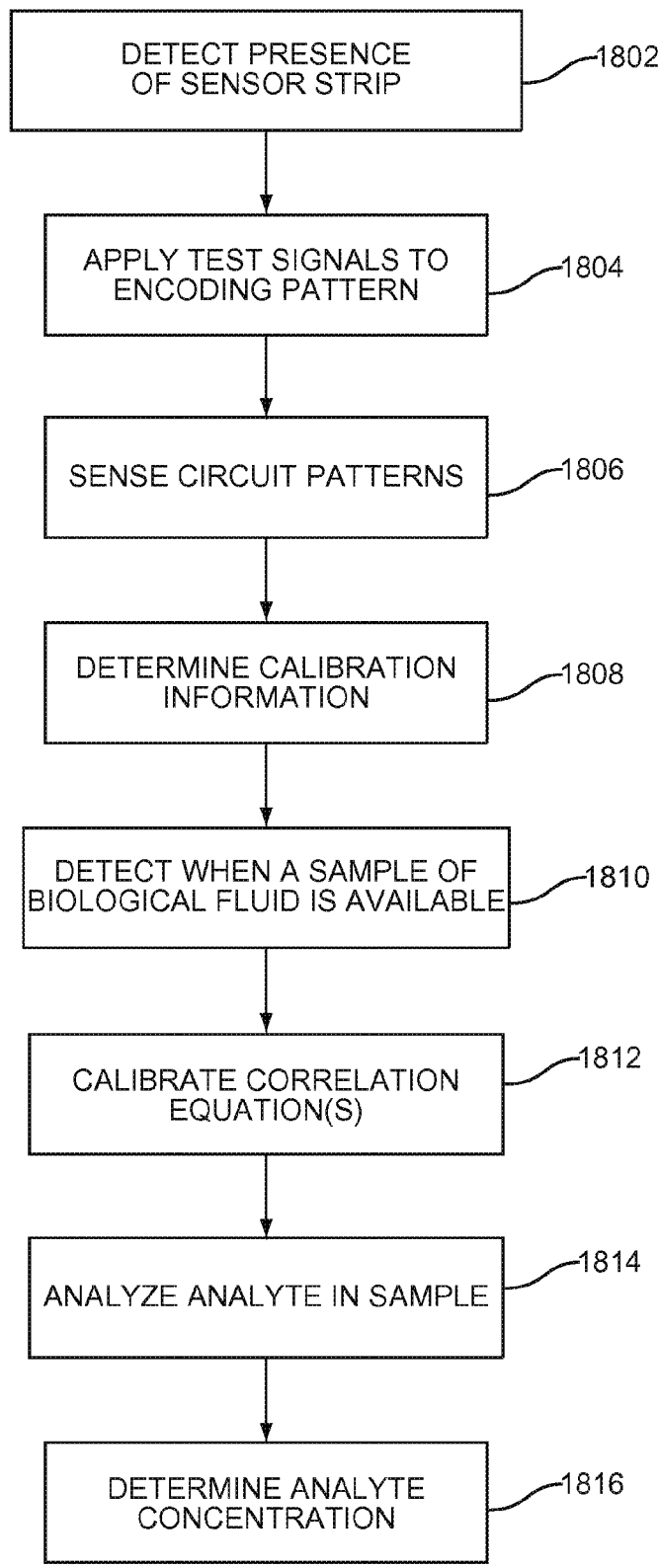
FIG. 18 represents another method for calibrating a biosensor.

FIG. 18 represents another method for calibrating an analysis of an analyte in a biological fluid. In 1802, a measuring device detects the presence of a sensor strip in a biosensor. In 1804, the measuring device applies test signals to an encoding pattern. In 1806, the measuring device senses circuit patterns on the encoding pattern. In 1808, the measuring device determines calibration information in response to the circuit patterns. In 1810, the measuring device detects when a sample of a biological fluid is available for analysis. In 1812, the measuring device calibrates one or more correlation equations in response to the calibration information. In 1814, the measuring device analyzes the analyte in the sample. In 1816, the measuring device determines the analyte concentration of the biological fluid using one or more calibrated correlation equations.

In 1802, the measuring device detects when a sensor strip is present. The measuring device may sense when a sensor strip is placed in the biosensor. The measuring device may sense when electrical contacts in the measuring device connect with electrical conductors and/or the encoding pattern on the sensor strip. The measuring device may apply a one or more signals to the working, counter, and/or other electrodes to detect when a sensor strip is present. The measuring device may apply a one or more signals to the encoding pattern to detect when a sensor strip is present. The measuring device may use other methods and devices to detect when a sensor strip is present in a biosensor.

In 1804, the measuring device applies test signals to an encoding pattern on a sensor strip, sensor strip package, or the like. The test signals may be generated optically or electrically. The measuring device selectively applies the test signals to the encoding pattern as previously discussed. The measuring device may apply the test signals in one or more steps or iterations.

In 1806, the measuring device senses the circuit patterns of at least two circuits on the encoding strip. The circuit patterns may be sensed optically or electrically as previously discussed. A pattern signal may be used to identify the circuit patterns on the encoding pattern.

In 1808, the measuring device determines the calibration information in response to the circuit patterns. The calibration information may be any information used to adjust correlation equations for electrochemical and/or optical analyses as previously discussed. The measuring device may select stored reference parameters and adjustments in response to a pattern or other signal indicating the circuit patterns on the encoding pattern.

In 1810, the measuring device detects when a sample of biological fluid is available for analysis. The measuring device may sense (mechanically, electrically, or the like) when electrical conductors in the sensor strip are in contact with a sample. The measuring device may apply one or more signals to the working, counter, and/or other electrodes to detect when a sample connects with the electrodes. The biosensor may use other methods and devices to detect when a sample is available for analysis.

In 1812, the measuring device calibrates one or more correlation equations in response to the calibration information. Correlation equations may be used to determine the analyte concentration in optical and/or electrochemical analyzes as previously discussed.

In 1814, the measuring device analyzes the analyte in the sample using an electrochemical analysis, an optical analysis, a combination thereof, or the like. In an electrochemical analysis, the measuring device may use one or more electrochemical processes as previously discussed. The measuring device measure and correlates an output signal from a redox reaction of the analyte with the analyte concentration. In an optical analysis, the measuring device measures the amount of light absorbed or generated by the reaction of a chemical indicator with the analyte as previously discussed. The measuring device measures and correlates the amount of light with the analyte concentration.

In 1816, the measuring device determines the analyte concentration in the sample of the biological fluid. The measuring device may use one or more of the calibrated correlation equations to determine the analyte concentration of the sample. The measuring device may use the calibrated analyte value or other result to determine the analyte concentration of the sample.

The biosensor system may be operated with sensor strips designed for a single analysis of the analyte concentration in the biological fluid. The biosensor system also allows a larger number of different calibration information to be used. The calibration may be implemented digitally, thus making the analyte analysis more tolerant of resistance differences between sensor strips from the manufacture of the encoding pattern and other resistance variations. A biosensor also may have more robust error detection of failures because all electrical contacts in the pattern read device must electrically or optically communicate with the corresponding contact areas of the circuits on the encoding pattern for accurate and precise sensing of the circuit patterns. The multiple circuits produced by the pattern on the sensor strip allows for inherent error checking of the coding information by enforcing rules regarding the total number circuits and the total number of isolated circuits. The biosensor may notify the user and may reject and/or eject the sensor strip when all the electrical contacts in the pattern read device do not electrically or optically communicated with the corresponding contact areas of the circuits on the encoding pattern. The error detection may reduce or eliminate misreads of the circuit patterns and the selection of incorrect calibration information, thus avoiding biased or incorrect analysis of the analyte concentration. The detection and reading of valid calibration patterns may be used to indicate the proper insertion of a sensor into the measurement device.

While various embodiments of the invention have been described, it will be apparent to those of ordinary skill in the art that other embodiments and implementations are possible within the scope of the invention.

The invention claimed is:

1. A biosensor system for determining an analyte concentration in a biological fluid, comprising:
   a measurement device having a processor connected to a pattern read device;
   a sensor strip including a counter electrode and a working electrode, the sensor strip further having an encoding pattern with at least two circuits, where each circuit forms a circuit pattern, and where each circuit pattern has a unique set of contact areas, each circuit pattern being separate from the counter electrode or the working electrode;
   where the measurement device and sensor strip implement an analyte analysis, where the analyte analysis has at least one correlation equation;
   where the pattern read device senses the at least two circuit patterns on the encoding pattern, the shape of the at least two circuit patterns corresponding to a mapping of a digital representation;
   where the processor determines calibration information responsive to the at least two circuit patterns;
   where the processor calibrates the at least one correlation equation responsive to the calibration information; and
   where the processor determines the analyte concentration responsive to at least one calibrated correlation equation.

2. The biosensor of claim 1, where the pattern read device selectively applies test signals to the encoding pattern.

3. The biosensor of claim 2, where the pattern read device drives at least one test signal to ground.

4. The biosensor of claim 3, where the pattern read device applies at least one other test signal at a pull-up voltage.

5. The biosensor of claim 3, where the pattern read device comprises a plurality of test circuits, where a first test circuit drives a first test signal to ground during a first step, and where a second test circuit drives a second test signal to ground during a second step.

6. The biosensor of claim 5, where a third test circuit drives a third test signal to ground during a third step.

7. The biosensor of claim 1, where each of the at least two circuits has at least two contact areas.

8. The biosensor of claim 1, where at least one of the at least two circuits has at least two contact areas and at least one of the at least two circuits has on contact area.

9. The biosensor of claim 1, where the test signals are current limited.

10. The biosensor of claim 9, where the test signals are less than about 50 µA.

11. The biosensor of claim 1, where the pattern read device generates a pattern signal responsive to the circuit patterns.

12. The biosensor of claim 1, where the at least two circuits include a first circuit, a second circuit, and at least one isolated circuit, where the first and second circuits each have at least two contact areas, and where the at least one isolated circuit has one contact area.

13. The biosensor of claim 1, where the processor checks for errors in the calibration information.

14. The biosensor of claim 13, where the processor enforces at least one rule regarding a total number of circuits and a total number of isolated circuits.

15. The biosensor of claim 13, where the processor determines whether a count of the circuit patterns matches the number of circuits on the encoding pattern.

16. The biosensor of claim 13, further comprising at least one of a predefined fixed number of isolated contacts on the encoding pattern and another predefined fixed number of circuits on the encoding pattern.

17. The biosensor of claim 13, where the processor determines whether one single contact circuit is detected.

18. A biosensor system for determining an analyte concentration in a biological fluid, comprising:
    a measurement device having a processor connected to a pattern read device, where the pattern read device has an array of electrical contacts;
    a sensor strip including a counter electrode and a working electrode, the sensor strip further having an encoding pattern with at least two circuits, where each circuit forms a circuit pattern, and where each circuit pattern has a unique set of contact areas, where the contact areas are in electrical communication with the electrical contacts, each circuit pattern being separate from the counter electrode or the working electrode;
    where the measurement device and sensor strip implement an analyte analysis, where the analyte analysis has at least one correlation equation;
    where the electrical contacts selectively apply test signals to the contact areas on the encoding pattern;
    where the pattern read device senses the at least two circuit patterns on the encoding pattern, the shape of the at least two circuit patterns corresponding to a mapping of a digital representation;
    where the processor determines calibration information responsive to the at least two circuit patterns;
    where the processor calibrates the at least one correlation equation responsive to the calibration information; and
    where the processor determines the analyte concentration responsive to at least one calibrated correlation equation.

19. The biosensor of claim 18, comprising an encoding pattern with a single-contact circuit and a multiple-contact circuit.

20. The biosensor of claim 18, comprising a pattern read device with a plurality of test circuits, where at least one of the test circuits drives a test signal to ground in response to a control signal from the processor.

21. The biosensor of claim 18, comprising an encoding pattern with a first circuit, a second circuit, and at least one isolated circuit.

22. The biosensor of claim 18, where the processor checks for errors in the calibration information, and where the processor enforces at least one rule regarding a total number of circuits and a total number of isolated circuits.

23. The biosensor of claim 18, where the processor checks for errors in the calibration information, and where the processor determines whether a count of the circuit patterns matches the number of circuits on the encoding pattern.

24. The biosensor of claim 18, where the processor checks for errors in the calibration information, and where the encoding pattern has at least one of a predefined fixed number of isolated contacts and another predefined fixed number of circuits.

25. The biosensor of claim 18, where the processor checks for errors in the calibration information, and where the processor determines whether one single contact circuit is detected.

26. A method for determining an analyte concentration in a biological fluid, comprising:

providing a sensor strip including a counter electrode and a working electrode, the sensor strip further including an encoding pattern with at least two circuits, each circuit forming a circuit pattern, each circuit pattern having a unique set of contact areas, each circuit pattern being separate from the counter electrode or the working electrode;

sensing the at least two circuit patterns on the encoding pattern, the shape of the at least two circuit patterns corresponding to a mapping of a digital representation;

determining calibration information in response to the at least two circuit patterns;

calibrating at least one correlation equation in response to the calibration information; and determining the analyte concentration in response to at least one calibrated correlation equation.

27. The method of claim 26, further comprising selectively applying test signals to the encoding pattern.

28. The method of claim 27, further comprising limiting the current of the test signals.

29. The method of claim 28, further comprising: applying test signals to the encoding pattern; and driving at least one test signal to ground.

30. The method of claim 26, further comprising checking for errors in the calibration information.

31. The method of claim 30, further comprising determining whether a count of the circuit patterns matches the number of circuits on the encoding pattern.

32. The method of claim 30, where the encoding pattern has at least one of a predefined fixed number of isolated contacts and another predefined fixed number of circuits.

33. The method of claim 30, further comprising detecting whether the encoding pattern has one single contact circuit.

* * * * *